(12) United States Patent
von Daehne et al.

(10) Patent No.: US 6,399,797 B1
(45) Date of Patent: Jun. 4, 2002

(54) VITAMIN D ANALOGUES

(75) Inventors: Welf von Daehne, Rungsted Kyst; Gunnar Grue-Sørensen, Roskilde; Martin John Calverley, Herlev; Claus Aage Svensgaard Bretting, Frederiksberg, all of (DK)

(73) Assignee: Leo Pharmaceutical Products Ltd. A/S (Løvens kemiske Fabrik Produktionsaktiesel skab), Ballerup (DK)

( * ) Notice: Subject to any disclaimer, the term of this patent is extended or adjusted under 35 U.S.C. 154(b) by 0 days.

(21) Appl. No.: 09/543,418

(22) PCT Filed: Oct. 2, 1998

(86) PCT No.: PCT/DK98/00423

§ 371 (c)(1),
(2), (4) Date: Apr. 5, 2000

(87) PCT Pub. No.: WO99/18070

PCT Pub. Date: Apr. 15, 1999

(30) Foreign Application Priority Data

Oct. 6, 1997 (GB) .............................. 9721156

(51) Int. Cl.[7] ........................ C07C 401/00; A61K 31/59
(52) U.S. Cl. ........................ 552/653; 552/653; 514/167
(58) Field of Search ........................ 552/653; 514/167

(56) References Cited

U.S. PATENT DOCUMENTS 5,545,633 A * 8/1996 Bretting .................... 514/167
5,929,056 A * 7/1999 Mourino et al. .......... 514/167

FOREIGN PATENT DOCUMENTS

| EP | 0 580 968 A2 | 2/1994 |
| EP | 0 717 034 A1 | 6/1996 |
| WO | 94/01398 | 1/1994 |
| WO | 95/12575 | 5/1995 |

* cited by examiner

Primary Examiner—Sabiha Qazi
(74) Attorney, Agent, or Firm—Pillsbury Winthrop LLP

(57) ABSTRACT

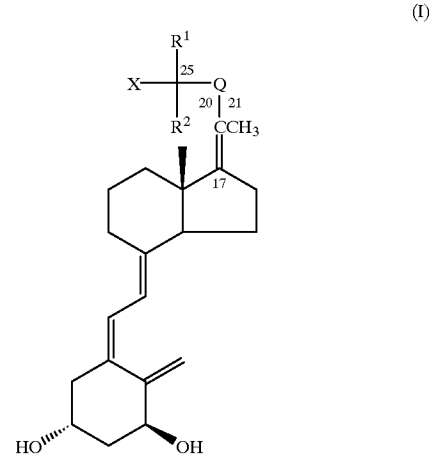

The present invention relates to compounds of formula (I), in which formula X is hydrogen or hydroxy or protected hydroxy; $R^1$ an $R^2$ stand for hydrogen, methyl or ethyl, or, when taken together with the carbon atom bearing the group X, $R^1$ and $R^2$ can form a $C_3$–$C_5$ carbocyclic ring; Q is a $C_3$–$C_6$ hydrocarbylene, hydrocarbylene indicating the diradical obtained after removal of 2 hydrogen atoms for a straight or banched, saturated or unsaturated hydrocarbon, in which one of any $CH_2$ groups may optionally be replaced by an oxygen atom or a carbonyl group, such that the carbon atom (C-22) directly bonded to C-20 is an $sp^2$ or $sp^3$ hybridized carbon atom, i.e. bonded to 2 or 3 other atoms; and in which another of the $CH_2$ groups may be replaced by phenylene, and where Q may optionally be substituted with one or more hydroxy or $C_1$–$C_4$-alkoxy groups. These compounds have been discovered to possess exceptionally high immunosuppressive activites together with high tumour cell proliferation inhibiting activities.

7 Claims, No Drawings

VITAMIN D ANALOGUES

This application is the national phase of international application PCT/DK98/00423 filed Oct. 2, 1998 which designated the U.S.

This invention relates to a hitherto unknown class of compounds that show strong activity in inducing differentiation and inhibiting undesirable proliferation of certain cells, including skin cells and cancer cells, as well as immunomodulating and anti-inflammatory effects, to pharmaceutical preparations containing these compounds, to dosage units of such preparations, and to their use in the treatment and/or prophylaxis of diseases characterised by abnormal cell differentiation and/or cell proliferation such as e.g. psoriasis and other disturbances of keratinisation, HIV-associated dermatoses, wound healing, cancer, including skin cancer, and of diseases of, or imbalance in, the immune system, such as host versus graft and graft versus host reaction and transplant rejection, and autoimmune diseases, such as discoid and systemic lupus erythematosus, diabetes mellitus and chronic dermatoses of autoimmune type, e.g. scieroderma and pemphigus vulgaris, and inflammatory diseases, such as rheumatoid arthritis, as well as a number of other disease states including hyperparathyroidism, particularly secondary hyperparathyroidism associated with renal failure, cognitive impairment or senile dementia (Alzheimer's disease) and other neurodegenerative diseases, hypertension, acne, alopecia, skin atrophy, e.g. steroid induced skin atrophy, skin ageing, including photo-ageing, and to their use for promoting osteogenesis and treating/preventing osteoporosis and osteomalacia.

The compounds of the invention constitute a novel class of vitamin D analogues represented by the general formula I:

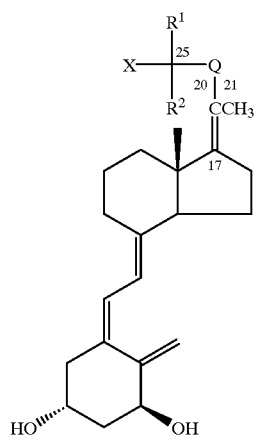

in which formula X is hydrogen or hydroxy or protected hydroxy; $R^1$ and $R^2$ stand for hydrogen, methyl or ethyl, or, when taken together with the carbon atom bearing the group X, $R^1$ and $R^2$ can form a $C_3$–$C_5$ carbocyclic ring; Q is a $C_3$–$C_6$ hydrocarbylene, hydrocarbylene indicating the diradical obtained after removal of 2 hydrogen atoms from a straight or branched, saturated or unsaturated hydrocarbon, in which one of any $CH_2$ groups may optionally be replaced by an oxygen atom or a carbonyl group, such that the carbon atom (C-22) directly bonded to C-20 is an $sp^2$ or $sp^3$ hybridised carbon atom, i.e. bonded to 2 or 3 other atoms; and in which another of the $CH_2$ groups may be replaced by phenylene, and where Q may optionally be substituted with one or more hydroxy or $C_1$–$C_4$-alkoxy groups.

Examples of I include, illustratively but not limitingly, the horizontal entries in Table 1 (p. 12), where for convenience Q is considered to be a composite of segments Qa through Qf, with any blank spaces being understood as direct bond, such that Qa is directly bonded to C-20, and $R^1$ is the same as $R^2$ unless otherwise noted. Thus, segments within Q such as methylene, methene (in contiguous pairs, i.e. carbon atoms connected by double bonds), methyne (in contiguous pairs, i.e. carbon atoms connected by triple bonds), phenylene (illustrated by m-phenylene), alkylidene (illustrated by 1,1-propylidene), hydroxymethylene, alkoxymethylene (illustrated by ethoxymethylene), keto, and oxa may be combined to produce side chains that are in fact identical (apart from the 17,20-double bond) to those already known from a variety of active vitamin D analogues.

The compounds of the invention can comprise more than one diastereoisomeric form (e.g. E or Z configuration of the 17,20-double bond and also of any non-ring double bond present in the group Q; R and S configurations when a hydroxy group or an alkoxy group or a branching atom is present in Q). The invention covers all these diastereoisomers in pure form and also mixtures thereof. In addition, prodrugs of I in which one or more of the hydroxy groups are masked as groups that can be reconverted to hydroxy groups in vivo could also be envisaged.

The compounds I may be obtained in crystalline form either directly by concentration from an organic solvent or by crystallisation or recrystallisation from an organic solvent or mixture of said solvent and a co-solvent which may be organic or inorganic, such as water. The crystals may be isolated in essentially solvent-free form or as a solvate, such as a hydrate. The invention covers all crystalline modifications and forms and also mixtures thereof.

A number of vitamin D analogues have been described that show some degree of selectivity in favour of the cell differentiation inducing/cell proliferation inhibiting activity in vitro as compared with the effects on calcium metabolism in vivo (as measured in increased serum calcium concentration and/or increased urinary calcium excretion), which adversely limit the dosage that can safely be administered. One of the first of these to appear, calcipotriol (INN) or calcipotriene (USAN), has been developed on the basis of this selectivity and is now recognised world-wide as an effective and safe drug for the topical treatment of psoriasis.

A study with another analogue selected on this basis supports the concept that systemically administered vitamin D analogues may inhibit breast cancer cell proliferation in vivo at sub-toxic doses (Colston, K. W. et al., Biochem. Pharmacol. 44, 2273–2280 (1992)).

Promising immunosuppressive activities of vitamin D analogues have been reviewed (Binderup, L., Biochem. Pharmacol. 43, 1885–1892 (1992)). Thus, a series of 20-epi-vitamin D analogues has been identified as potent inhibitors of T-lymphocyte activation in vitro (Binderup, L. et al, Biochem. Pharmacol. 42, 1569–1575 (1991)). Two of these analogues, MC 1288 and KH 1060, systemically administered, have shown immunosuppressive activities in vivo in experimental animal models. Additive or synergistic effects were observed in combination with low-dose cyclosporin A. KH 1060, alone or in combination with cyclosporin A, has also been shown to prevent autoimmune destruction of transplanted islets in diabetic NOD mice (non-obese diabetic mice) (Bouillon, R. et al. In: Vitamin D, Proceedings of the Ninth Workshop on Vitamin D, Orlando, Fla., Walter de Gruyter, Berlin, 1994, pp 551–552). MC 1288 was able to prolong survival of cardiac and small bowel grafts in rats (Johnsson, C. et al. In: Vitamin D, Proceedings of the Ninth Workshop on Vitamin D, Orlando, Fla., Walter de Gruyter, Berlin, 1994, pp 549–550). However, in all these studies, the dosages of the analogues that produced significant immunosuppression also induced increases in serum calcium levels. There is therefore a continuing need for new analogues with high potency showing an acceptable combination of prolonged therapeutic activity and minimum toxic effects.

The present invention provides a hitherto undisclosed series of vitamin D analogues which is characterised by the presence of a double bond between C-17 and C-20.

21-Nor-17(20)-ene vitamin D analogues are described in EP 0 717 034, but the only previously described vitamin D analogues with a C-17,20 double bond and the C-21 methyl group preserved are those with a C-22,23 triple bond (WO 94/01398). The compounds of the present invention extend the range of side chain types to comprise a more comprehensive selection of side chains known from prior art vitamin D analogues.

These compounds have been discovered to possess exceptionally high immunosuppressive activities together with high tumour cell proliferation inhibiting activities.

The following standard abbreviations are used throughout this disclosure:

18C6=18-Crown-6
AIBN=2,2'-azobisisobutyronitrile
b.p.=boiling point
Bu=n-butyl
Bu$^t$=tert-butyl
DIBAH=diisobutylaluminium hydride
DMAP=4-dimethylaminopyridine
DMF=N,N-dimethylformamide
DMR=Dess-Martin-Reagent=1,1,1-triacetoxy-1,1-dihydro-1,2-benz-iodoxol-3(1H)-one
Et=ethyl
Ether=diethyl ether
Fg=functional group
LDA=lithium diisopropylamide
Lg=leaving group
Me=methyl
m.p.=melting point
PCC=pyridinium chlorochromate
PDC=pyridinium dichromate
Ph=phenyl
PPTS=pyridinium p-toluenesulfonate
Py=pyridine
r.o.s.="rest of sequence"
TBABr=tetra-n-butylammonium bromide
TBAF=tetra-n-butylammonium fluoride
TBAOH=tetra-n-butylammonium hydroxide
TBAHSO$_4$=tetra-n-butylammonium hydrogensulfate
TBS=tert-butyldimethylsilyl
Tf=trifluromethansulfonyl
TFA=trifluoroacetic acid
THF=tetrahydrofuran
THP=tetrahydro-4H-pyran-2-yl
TMS=trimethylsilyl
Tol=toluene
Ts=4-toluenesulfonyl Compounds of formula I, as illustrated in Table 1, may be prepared by the general methods of Schemes 1 and 3. In Scheme 1, the vitamin D nucleus building block aldehyde Ia, is converted to a key intermediate of type II (Scheme 2) via the intermediates 2, 3 or 4.

Scheme 1

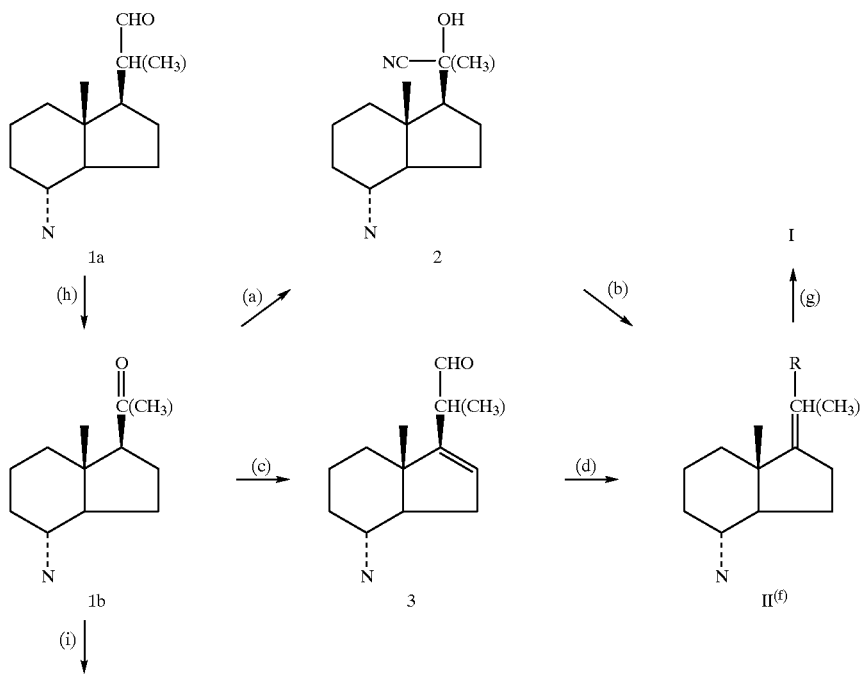

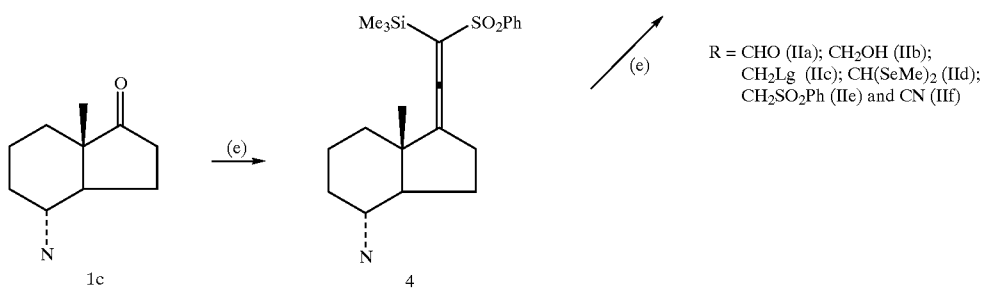

R = CHO (IIa); CH₂OH (IIb); CH₂Lg (IIc); CH(SeMe)₂ (IId); CH₂SO₂Ph (IIe) and CN (IIf)

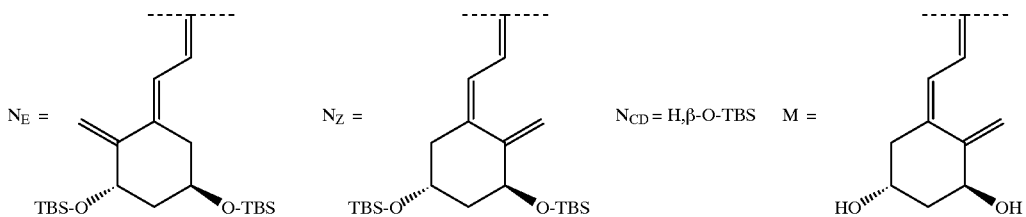

Notes to Scheme 1
(a) HCN
(b) 1) POCl₃/Py→IIf; 2) DIBAH→IIa
(c) W. von Daehne et al., poster at X vit. D workshop, Strasbourg 1997; WO 98/24762
(d) NaOH, CH₂Cl₂, TBABr→IIa
(e) Cf. N. Ohmori et al., Tetr. Lett. 1986, 27, 71
(f) For IIb, IIc, IId and IIe: See Scheme 2

Clinical Application; Norman, A. W., Bouillon, R., Thomasset, M., Eds.; de Gruyter, Berlin, 1991, pp 161–162
(i) Fernandez et al., J.Org.Chem. 1992, 57, 3173

In Scheme 2 the method of preparation of each type of compound II, that is IIa, IIb, IIc, IId, and IIe from compound 2, 3 and 4 is outlined. In Table 2 and preparations 1 to 6, 10, 18, 31 and 34 the synthesis of some compounds of types IIa, IIb and IIc are described in more detail.

Scheme 2

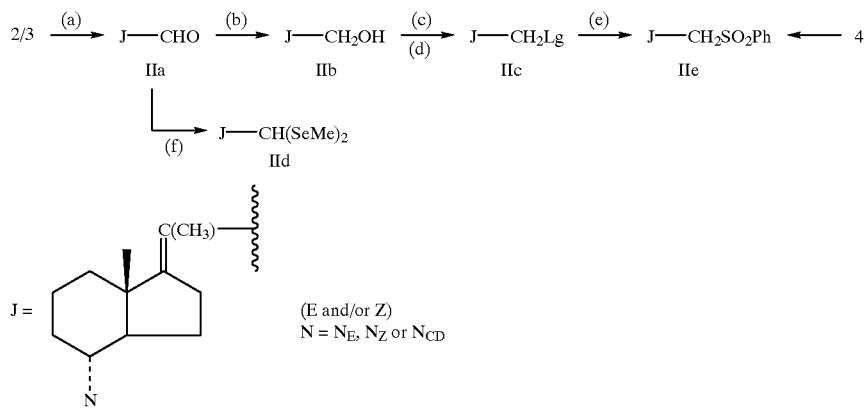

(g) See Scheme 3, Table 1, and "Methods of Synthesis 1–7"
(h) 1b (N=N$_{CD}$): B. Fernandez et al., J.Org.Chem. 1992, 57, 3173 1b (N=N$_E$): K. Hansen et al., in: Vitamin D: Gene Regulation, Structure-Function Analysis and Notes to Scheme 2

(a) See Table 2, Preparations 1–4, and 31.
(b) NaBH₄/CeCl₃

(c) Lg=leaving groups, such as e.g. halide (Cl, Br, I), lower alkanoate, p-toluenesulfonate (tosylate), methanesulfonate (mesylate) or trifluoromethanesulfonate (triflate).

(d) The compounds IIc are obtained from IIb by standard procedures using suitable acid derivatives corresponding to the required Lg.

(e) 1) PhS⁻-K⁺, 2) H$_2$O$_2$, NaWO$_4$ (M. J. Calverley, in: Trends in Medicinal Chemistry '90; S. Sarel et al. Eds., Blackwell Scientific Publ., Oxford 1992, pp 299–306).

(f) B(SeMe)$_3$, TFA, CH$_2$Cl$_2$, (WO 89/10351; M. J. Calverley, Tetr. Lett. 1987, 28, 1337).

In Scheme 3 the synthesis of compounds I from the key intermediates II (a–e) is outlined in a general manner. More detailed descriptions for the synthesis of the preferred compounds I, listed in Table 1, are given in the "Methods of synthesis 1–7", and in further detail in the Preparations (Table 3) and Examples (Table 4).

Scheme 3

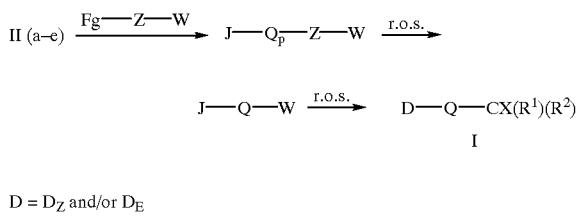

D = D$_Z$ and/or D$_E$

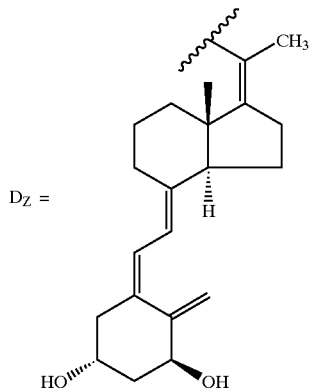

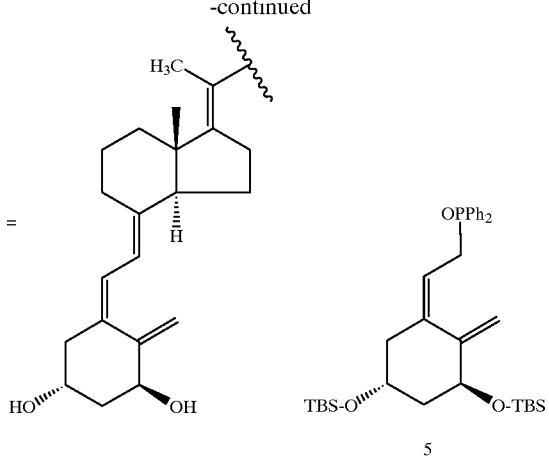

Compounds II are first reacted with side chain building blocks Fg—Z—W, to give the intermediates J—Q$_p$—Z—W. Fg is a reactive functional group, the kind of which is indicated in the Methods of synthesis 1–7; Z is a linking group, which together with Q$_p$ forms a side chain moiety which may either be identical to Q in compound I, or alternatively may be a moiety which can be converted to Q at any subsequent stage in the synthesis; Q$_p$ is a part of Q which may either be identical to Qa, or to Qa,Qb, or to Qa,Qb,Qc, depending on the particular method of synthesis, or Q$_p$ may similarly be converted to Qa, or to Qa,Qb, or to Qa,Qb,Qc later during the synthesis; W is either identical to the group CX(R$^1$)(R$^2$) in compound I, or may be similarly converted thereto later during the synthesis.

The remaining steps in the synthesis involve the below mentioned operations 1–4, in the following called "rest of sequence", abbreviated "r.o.s."; these operations may be performed in any desired order, according to the synthetic demands of each particular Compound I to be prepared:

1 Optional conversion of the group Q$_p$—Z to Q;
2 Optional conversion of the group W to C(R$^1$)(R$^2$)(X).
3 Optional conversion of the group N$_E$/N$_{CD}$ to the group N$_Z$ by:
   a Triplet-sensitised photoisomerisation of the vitamin D triene (5E to 5Z); or
   b Desilylation, oxidation to the ketone and Horner coupling with the A-ring building block 5 of Scheme 3 (see e.g. WO 94/14766);
4 Conversion of the group N$_Z$ to the group M by removal of the vitamin D nucleus silyl protective groups.

TABLE 1

Preferred Compounds I

| Qa | Qb | Qc | Qd | Qe | Qf | R1/R2 | X | Method |
|---|---|---|---|---|---|---|---|---|
| CH2 | CH2 | CH2 | | | | Me | H | 1 |
| CH2 | CH2 | CH2 | | | | Me | OH | 1 |
| CH | CH | CH2 | | | | Et | OH | 5 |
| CH2 | O | CH2 | | | | Et | OH | 7 |
| CH(OH) | CH2 | CH2 | | | | Me | OH | 2 |
| CH(OH) | CH | CH | | | | Me | OH | 3 |
| CH | CH | CH(OH) | | | | (CH2)2 | H | 5 |
| CH(OH) | C | C | | | | Et | OH | 4 |
| CH(OC2H5) | CH2 | CH2 | | | | Et | OH | 2 |
| CH(OC2H5) | CH | CH | | | | Me | OH | 3 |

TABLE 1-continued

Preferred Compounds I

| Qa | Qb | Qc | Qd | Qe | Qf | R1/R2 | X | Method |
|---|---|---|---|---|---|---|---|---|
| CH(OC2H5) | C | C | | | | Et | OH | 4 |
| C(=O) | CH2 | CH2 | | | | Me | OH | 2 |
| C(=O) | CH | CH | | | | Me | OH | 3 |
| C(=O) | C | C | | | | Et | OH | 4 |
| CH2 | CH2 | CH2 | CH2 | | | Et | OH | 1 |
| CH | CH | CH2 | CH2 | | | Me | OH | 5 |
| CH | CH | CH | CH | | | Et | OH | 6 |
| CH | CH | C | C | | | Et | OH | 5 |
| CH2 | O | CH2 | CH2 | | | Et | OH | 7 |
| CHOH | CH2 | CH2 | CH2 | | | H | H | 2 |
| CH(OH) | CH2 | CH2 | CH2 | | | Et | OH | 2 |
| CH(OH) | CH | CH | CH2 | | | Et | OH | 3 |
| CH(OH) | C | C | CH2 | | | Et | OH | 4 |
| CH(OC2H5) | CH2 | CH2 | CH2 | | | Et | OH | 2 |
| CH(OC2H5) | CH | CH | CH2 | | | Et | OH | 3 |
| CH(OC2H5) | C | C | CH2 | | | Et | OH | 4 |
| CH(OC2H5) | C | C | CH2 | | | Et | OTHP | 4 |
| C(=O) | CH2 | CH2 | CH2 | | | Et | OH | 2 |
| C(=O) | CH | CH | CH2 | | | Et | OH | 3 |
| C(=O) | C | C | CH2 | | | Et | OH | 4 |
| CH2 | CH2 | CH2 | CH2 | CH2 | | Me | OH | 1 |
| CH | CH | CH2 | CH2 | CH2 | | Me | OH | 5 |
| CH | CH | CH | CH | CH2 | | Me | OH | 6 |
| CH2 | O | CH2 | CH2 | CH2 | | Me | OH | 7 |
| CH2 | O | CH2 | CH2 | CH2 | | Et | OH | 7 |
| CH | CH | CH2 | O | CH2 | | Me | OH | 5 |
| CH(OH) | CH2 | CH2 | CH2 | CH2 | | Me | OH | 2 |
| CH(OH) | CH | CH | CH2 | CH2 | | Me | OH | 3 |
| CH(OH) | C | C | CH2 | CH2 | | Me | OH | 4 |
| CH(C2H5) | O | CH2 | CH2 | CH2 | | Et | OH | 7 |
| CH(OC2H5) | CH2 | CH2 | CH2 | CH2 | | Me | OH | 2 |
| CH(OC2H5) | CH | CH | CH2 | CH2 | | Me | OH | 3 |
| CH(OC2H5) | C | C | CH2 | CH2 | | Me | OH | 4 |
| C(=O) | CH2 | CH2 | CH2 | CH2 | | Me | OH | 2 |
| C(=O) | CH | CH | CH2 | CH2 | | Me | OH | 3 |
| C(=O) | C | C | CH2 | CH2 | | Me | OH | 4 |
| CH2 | O | m-C6H4 | | | | Me | OH | 7 |
| CH2 | O | CH2 | m-C6H4 | | | Me | OH | 7 |
| CH2 | CH2 | CH2 | CH2 | CH2 | CH2 | Me | OH | 1 |

Note to Table 1

The compounds may have either 17(20)E or 17(20)Z-configuration, both configurations are included. For compounds with a 22-OH or 22-OR$^3$ substituent, both 22R and 22S configurations are included. For compounds with double bonds at C-22, C-23 or C-24, both the E and Z configurations are included.

Methods of Synthesis: 1–7

The methods described in the following are based on procedures described for the preparation of vitamin D analogues having a 17β,20-single bond with either "20-normal" or "20-epi" configuration instead of the 17,20-double bond of the compounds of the present invention.

Reference is given to this prior art, in which experimental details can be found.

The following definitions are used:

R$^3$=C$_1$–C$_5$ alkyl; Y=Halogen. Other symbols and abbreviations have the above meanings.

Abstracts of the paper and posters, presented at the Tenth Workshop on Vitamin D, Strasbourg, France—May 24–29, 1997, which are mentioned in this application, are published:

a) Bretting, C. et al., pp. 77–78;
b) Calverley, M. et al., pp. 30–31;
c) Hansen, K. et al., pp. 87–88;
d) von Daehne, W. et al., pp. 81–82 in Vitamin D: Chemistry, Biology and Clinical Applications of the Steroid Hormone (Editors Norman, A. W.; Bouillon, R.; Thomasset, M.), University of California, Riverside, 1997.

Method 1

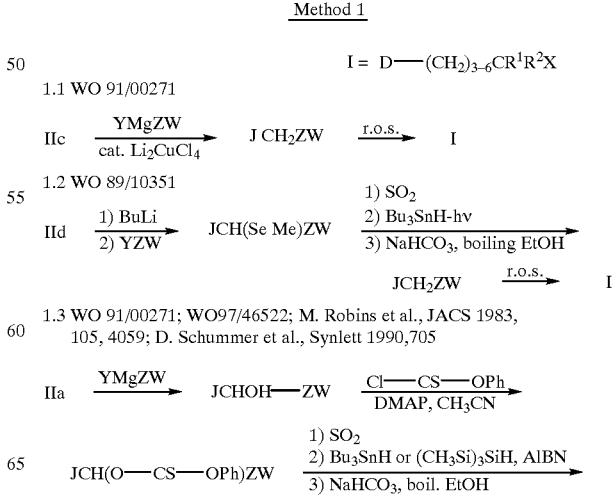

1.1 WO 91/00271

1.2 WO 89/10351

1.3 WO 91/00271; WO97/46522; M. Robins et al., JACS 1983, 105, 4059; D. Schummer et al., Synlett 1990,705

-continued $$J-CH_2-Z-W \xrightarrow{r.o.s.} I$$

Method 2

$$I = D-C^{22}(H, OH/H, OR^3/O)-(CH_2)_{2-5}-CR^1R^2-X$$

WO 91/00271; WO 97/46522; C. Bretting et al., poster at X vit. D workshop, Strasbourg, 1997

$$IIa \xrightarrow{YMg-Z-W} J-CHOH-Z-W \quad (a) \xrightarrow{r.o.s.} I$$

Method 3

$$I = D-C^{22}(H, OH/H, OR^3/O)-CH=CH-(CH_2)_{0-2}-CR^1R^2-X$$

3.1.1 WO 98/18759

$$IIa \xrightarrow{CH=CH-MgY} J-CHOH-CH=CH_2 \xrightarrow[2,6\text{ lutidine}]{TBSOTf}$$

$$J-CH(OTBS)-CH=CH_2 \xrightarrow[\substack{1)\ SO_2 \\ 2)\ O_3 \\ 3)\ Ph_3P \\ 4)\ EtOH,\ NaHCO_3,\ 80°}]{}$$

$$J-CH(OTBS)CHO \xrightarrow{Ph_3P^+-CH_2^--COOCH_3}$$

$$J-CH(OTBS)CH=CH-COOCH_3 \xrightarrow{1.\ R^1Li\ \text{or}\ R^1MgY}$$

$$J-CH(OTBS)CH=CH-CR_2^1OH \xrightarrow{r.o.s.}$$

$$I\ (C^{22}-OH;\ (CH_2)_0;\ X = O)$$

3.1.2. As 3.1.1., but instead of silylation of $C^{22}OH$ in step 2, this group is alkylated to $C^{22}OR^3$ or oxidized to $C^{22}O$ as described in note (a) to give finally $I\ (C^{22}-OR^3\ \text{or}\ C^{22}O;\ (CH_2)_0;\ X = O)$ 3.2.

$$IIa \xrightarrow{YMgCH=CH-Z-W}$$

$$J-CHOH-CH=CH-Z-W \quad (a) \xrightarrow{r.o.s.} I$$

3.3

$$IIa \xrightarrow{Me_3SiCN} J-CH(OSiMe_3)CN \xrightarrow{DIBAH}$$

$$J-CH(OSiMe_3)-CHO \xrightarrow{Ph_3P^+-CH_2^--Z-W} (b)$$

$$J-C(OSiMe_3)=CH-CH-Z-W \quad (c) \xrightarrow{r.o.s.} I$$

Method 4

$$I = D-C^{22}(H, OH/H, OR^3/O)C\equiv C-(CH_2)_{0-2}-CR^1R^2-X$$

WO 93/19044

$$IIa \xrightarrow{LiC\equiv C-Z-W}$$

$$J-CHOH-C\equiv C-Z-W \quad (a) \xrightarrow{r.o.s.} I$$

Method 5

$$I = D-C^{22}H=CH-Z-CR^1R^2-X$$

5.1.1 WO 87/00834

$$IIa \xrightarrow{Ph_3P^+-CH^--CO-C(CH_2)_2} (b)$$

$$J-CH=CH-CO-CH(CH_2)_2 \xrightarrow{NaBH_4 / CeCl_3}$$

$$J-CH=CH-CHOH-CH(CH_2)_2 \xrightarrow{r.o.s.}$$

$$I = D-CH=CH-CHOH-CH(CH_2)_2$$

5.1.2 (e.g. WO 95/02577)

$$IIa \xrightarrow{Ph_3P^+-CH^--Z-W} (b)$$

$$J-CH=CH-Z-W \xrightarrow{r.o.s.} I$$

5.2 WO 91/00271

$$IIa \xrightarrow[\substack{2)\ PhCOCl, \\ 3)\ Na/Hg}]{1)\ Ph-SO_2-CH_2-Z-W,\ LDA}$$

$$J-CH=CH-Z-W \xrightarrow{r.o.s.} I$$

5.3 M.J. Calverley, in: Trends in Medicinal Chemistry '90; S. Sarel et al. Eds.; Blackwell Scientific Publ., Oxford 1992, p. 299–306.

$$IIe \xrightarrow[\substack{1)\ LDA, \\ 2)\ OHC-Z-W \\ 3)\ PhCOCl, \\ 4)\ Na/Hg}]{}$$

$$J-CH=CH-Z-W \xrightarrow{r.o.s.} I$$

5.4

$$IIa \xrightarrow{YMgCH_2ZW} J-CHOH-CH_2Z-W \xrightarrow{\text{Dehydration}} (d)$$

$$J-CH=CH-Z-W \xrightarrow{r.o.s.} I$$

5.5 WO 94/10139

$$IIa \xrightarrow[\substack{1)\ Ph_3P^+-CH_2^--COOMe \\ 2)\ DIBAH}]{}$$

$$J-CH=CH-CH_2-OH \xrightarrow[\substack{2)\ R^1MgY}]{1)\ BrCH_2COO-Bu^t,\ KOH,\ TBAHSO_4}$$

$$J-CH=CH-CH_2-O-CH_2-CR_2^1-OH \xrightarrow{r.o.s.}$$

$$I = D-CH=CH-CH_2-O-CH_2-CR_2^1-OH$$

Method 6

$$I = D\overset{22}{\diagdown}\overset{}{=}\overset{23}{\diagup}\overset{}{=}(CH_2)_{0-1}-CR^1R^2-X$$

6.1.1 WO 91/00855

$$IIa \xrightarrow{Ph_3P^+-CH^--CH=CH-COOMe}$$

$$J-CH=CH-CH=CH-COOMe \xrightarrow{R^1Li}$$

$$J-CH=CH-CH=CH-CR_2^1-OH \xrightarrow{r.o.s.}$$

$$I = D-CH=CH-CH=CH-CR_2^1-OH$$

6.1.2 WO 91/00855

$$IIa \xrightarrow[\substack{1)\ Ph_3P^+-CH_2^--COOMe \\ 2)\ DIBAH, \\ 3)\ PDC}]{}$$

$$J-CH=CH-CHO \xrightarrow[\substack{2)\ PhCOCl \\ 3)\ Na/Hg}]{1)\ PhSO_2-CH_2CH_2-CR^1R^2-X,\ LDA}$$

$$J-CH=CH-CH=CH-CH_2-CR^1R^2-X \xrightarrow{r.o.s.}$$

$$I = D-CH=CH-CH=CH-CH_2-CR^1R^2-X$$

-continued 6.2 A. Fürstner, Synth. 1989, 571; Y. Shen et al.,Tetr. Lett. 1988, 29, 6119

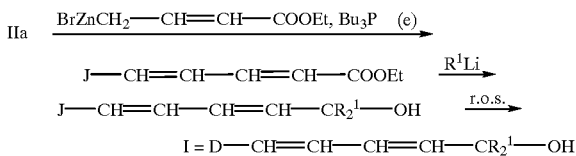

Method 7

$$I = D\text{---}CH(H/R^3)\text{---}O\text{---}Z\text{---}CR^1R^2\text{---}X$$

7.1 WO 91/15475

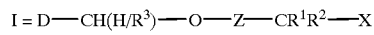

7.2

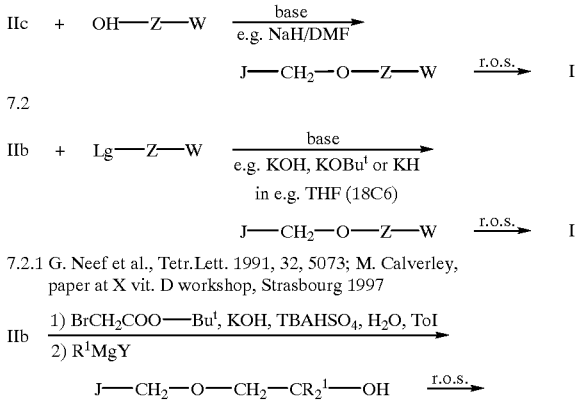

7.2.1 G. Neef et al., Tetr.Lett. 1991, 32, 5073; M. Calverley, paper at X vit. D workshop, Strasbourg 1997

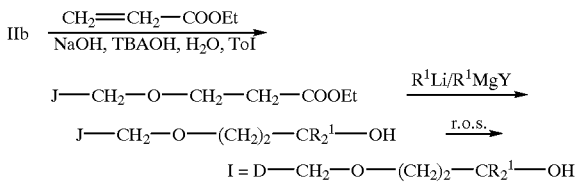

7.2.2 N. Kubodera et al., Chem.Pharm,Bull. 1992, 40, 1494

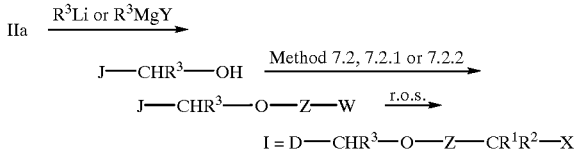

7.3 K. Hansen et al., poster at X vit. D workshop, Strasbourg, 1997

IIa $\xrightarrow{R^3Li \text{ or } R^3MgY}$

J—CHR³—OH $\xrightarrow{\text{Method 7.2, 7.2.1 or 7.2.2}}$

J—CHR³—O—Z—W $\xrightarrow{\text{r.o.s.}}$

I = D—CHR³—O—Z—CR¹R²—X

Notes to Methods of Synthesis: 1–7

(a) Optional alkylation of $C^{22}$—OH to $C^{22}$—OR³ e.g. with
    R³Y + KH + 18C6 as in WO 93/19044 or WO 97/46522 or oxidation of
    $C^{22}$—OH to $C^{22}$=O, e.g. with PCC or DMR, as in WO 97/20811.
(b) Optionally other Wittig-type reagents such as $(EtO)_2PO$—$CH_2$—Z—W +
    base or $Ph_2PO$—$CH_2$—Z—W + base may be used.
(c) Optional desilylation of $C^{22}$—$OSiMe_3$ to $C^{22}$—OH followed by alkylation or
    oxidation as described in note (a).
(d) Standard methods of dehydration, such as acid catalysed dehydration, or
    treatment with $POCl_3$/pyridine, or treatment with "Martin sulfurane dehydrating
    agent" may be used.
(e) Alternatively the tributylphosphine may be excluded, resulting in a 22-ol. This
    may be dehydrated to the 22,23-ene in a separate step, by standard methods,
    see e.g. M.W. Rathke, Org. React. 1975 22, 432.

The present compounds are intended for use in pharmaceutical compositions which are useful in the local or systemic treatment of human and veterinary disorders as described above.

The present compounds may be used in combination with other pharmaceuticals or treatment modalities. In the treatment of psoriasis the present compounds may be used in combination with e.g. steroids or with other treatments e.g. light- or UV-light-treatment or the combined PUVA-treatment. In the treatment of cancer the present compounds may be used in combination with other anti-cancer drugs or anti-cancer treatments, such as radiation treatment. In the prevention of graft rejection and graft versus host reaction, or in the treatment of auto-immune diseases, the present compounds may advantageously be used in combination with other immunosuppressive/immunoregulating drugs or treatments, e.g. with cyclosporin A.

The amount required of a compound of formula I (hereinafter referred to as the active ingredient) for therapeutic effect will, of course, vary both with the particular compound, the route of administration and the mammal under treatment. The compounds of the invention can be administered by the parenteral, intra-articular, enteral or topical routes. They are well absorbed when given enterally and this is the preferred route of administration in the treatment of systemic disorders. In the treatment of dermatological disorders like psoriasis or eye diseases topical or enteral forms are preferred.

While it is possible for an active ingredient to be administered alone as the raw chemical, it is preferable to present it as a pharmaceutical formulation. Conveniently, the active ingredient comprises from 0.1 ppm to 0.1% by weight of the formulation.

The formulations, both for veterinary and for human medical use, of the present invention thus comprise an active ingredient in association with a pharmaceutically acceptable carrier therefore and optionally other therapeutic ingredient (s). The carrier(s) must be "acceptable" in the sense of being compatible with the other ingredients of the formulations and not deleterious to the recipient thereof.

The formulations include e.g. those in a form suitable for oral, ophthalmic, rectal, parenteral (including subcutaneous, intramuscular and intravenous), transdermal, intra-articular and topical, nasal or buccal administration.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

Formulations for rectal administration may be in the form of a suppository incorporating the active ingredient and a carrier, or in the form of an enema.

Formulations suitable for parenteral administration conveniently comprise a sterile oily or aqueous preparation of the active ingredient which is preferably isotonic with the blood of the recipient. Transdermal formulations may be in the form of a plaster.

Formulations suitable for intra-articular or ophthalmic administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops.

Formulations suitable for administration to the nose or buccal cavity include powder, self-propelling and spray formulations, such as aerosols and atomisers.

In addition to the aforementioned ingredients, the formulations of this invention may include one or more additional ingredients, such as diluents, binders, preservatives etc.

The compositions may further contain other therapeutically active, compounds usually applied in the treatment of the above mentioned pathological conditions, such as other immunosuppressants in the treatment of immunological diseases, or steroids in the treatment of dermatological diseases.

The present invention further concerns a method for treating patients suffering from one of the above pathological conditions, said method consisting of administering to a patient in need of treatment an effective amount of one or more compounds of formula I, alone or in combination with one or more other therapeutically active compounds usually applied in the treatment of said pathological conditions. The treatment with the present compounds and/or with further therapeutically active compounds may be simultaneous or with intervals.

In the systemic treatment daily doses of from 0.001–2 µg per kilogram bodyweight, preferably from 0.002–0.3 µg/kg of mammal bodyweight, for example 0.003–0.2 µg/kg of a compound of formula I are administered, typically corresponding to a daily dose for an adult human of from 0.2 to 15 µg. In the topical treatment of dermatological disorders, ointments, creams or lotions containing from 0.1–500 µg/g, and preferably from 0.1–100 µg/g, of a compound of formula I are administered. For topical use in ophthalmology ointments, drops or gels containing from 0.1–500 µg/g, and preferably from 0.1–100 µg/g, of a compound of formula I are administered. The oral compositions are formulated, preferably as tablets, capsules, or drops, containing from 0.05–50 µg, preferably from 0.1–25 µg, of a compound of formula I, per dosage unit.

The invention is further illustrated by the following non-limiting General Procedures, Preparations and Examples:

GENERAL PROCEDURES, PREPARATIONS AND EXAMPLES

The exemplified compounds I are listed in Table 4, the intermediates of general formula II are listed in Table 2, and other intermediates are listed in Table 3.

General:

THF was dried over sodium/benzophenone. Reactions were routinely run under an argon atmosphere unless otherwise noted. In the standard work-up procedure, the organic layer was separated, washed with water and saturated sodium chloride solution, dried over anhydrous magnesium sulfate, and concentrated in vacuo to give the product, which was purified by chromatography or crystallisation.

For $^1$H nuclear magnetic resonance spectra (300 MHz) and $^{13}$C NMR (75.6 MHz) chemical shift values (δ) (in ppm) are quoted, for deuteriochloroform solutions relative to internal tetramethylsilane (δ=0.00) or chloroform (δ=7.25) or deuteriochloroform (δ=76.81 for $^{13}$C NMR). The value for a multiplet, either defined (doublet (d), triplet (t), quartet (q)) or not (m) at the approximate mid point is given unless a range is quoted (s=singlet, b=broad).

TABLE 2

Some compounds of type II

| Formula | N | Config. at 17, 20 | Comp. Type | Comp. No. | Prep. No. |
|---|---|---|---|---|---|
| J—CHO | $N_E$ | Z | IIa | 201 | 1, 2 |
| J—CHO | $N_E$ | E | IIa | 202 | 1, 2, 4 |
| J—CH$_2$OH | $N_E$ | Z | IIb | 203 | 5 |
| J—CH$_2$OH | $N_E$ | E | IIb | 204 | 6 |
| J—CH$_2$OOCC(CH$_3$)$_3$ | $N_E$ | Z | IIc | 205 | 10 |
| J—CH$_2$OOCC(CH$_3$)$_3$ | $N_E$ | E | IIc | 206 | 18 |
| J—CN | $N_E$ | E | IIf | 211 | 3 |
| J—CN | $N_E$ | Z | IIf | 212 | 3 |
| J—CHO | $N_Z$ | Z | IIa | 207 | 31 |
| J—CH$_2$Cl | $N_E$ | Z | IIc | 208 | 34 |

J: See Scheme 2
N ($N_E$/$N_Z$): See Scheme 1

TABLE 3

Some intermediate products

| Formula | N | Config. at 17(20) | Config. at C22 (A or B) | Comp. No. | Prep. No. |
|---|---|---|---|---|---|
| J—CHOH—C$_4$H$_9$ | $N_E$ | Z | A | 301 | 7 |
| J—CHOH—C$_4$H$_9$ | $N_E$ | Z | B | 302 | 7 |
| J—CHOH—C$_4$H$_9$ | $N_Z$ | Z | A | 401 | 8 |
| J—CHOH—C$_4$H$_9$ | $N_Z$ | Z | B | 402 | 9 |
| J—(CH$_2$)$_3$CH(CH$_3$)$_2$ | $N_E$ | Z | | 303 | 11 |
| J—(CH$_2$)$_3$CH(CH$_3$)$_2$ | $N_Z$ | Z | | 403 | 12 |
| J—CHOH—C≡C—CH$_2$—C(C$_2$H$_5$)$_2$OTHP | $N_E$ | Z | A | 304 | 13 |
| J—CHOH—C≡C—CH$_2$—C(C$_2$H$_5$)$_2$OTHP | $N_E$ | Z | B | 305 | 13 |
| J—CHOH—C≡C—CH$_2$—C(C$_2$H$_5$)$_2$OTHP | $N_Z$ | Z | A | 404 | 14 |
| J—CHOH—C≡C—CH$_2$—C(C$_2$H$_5$)$_2$OTHP | $N_Z$ | Z | B | 405 | 15 |
| J—CHOC$_2$H$_5$—C≡C—CH$_2$C(C$_2$H$_5$)$_2$OTHP | $N_Z$ | Z | A | 406 | 16 |
| J—CHOC$_2$H$_5$—C≡C—CH$_2$C(C$_2$H$_5$)$_2$OTHP | $N_Z$ | Z | B | 407 | 17 |
| J—(CH$_2$)$_3$C(CH$_3$)$_2$—OTMS | $N_E$ | Z | | 308 | 19 |
| J—(CH$_2$)$_3$C(CH$_3$)$_2$—OTMS | $N_E$ | E | | 309 | 20 |
| J—(CH$_2$)$_3$C(CH$_3$)$_2$OH | $N_E$ | Z | | 408 | 21 |
| J—(CH$_2$)$_3$C(CH$_3$)$_2$OH | $N_E$ | E | | 409 | 22 |
| J—(CH$_2$)$_3$C(CH$_3$)$_2$OH | $N_Z$ | Z | | 508 | 23 |
| J—(CH$_2$)$_3$C(CH$_3$)$_2$OH | $N_Z$ | E | | 509 | 24 |
| HC≡C—CH$_2$—C(C$_2$H$_5$)$_2$—OSiMe$_3$ | | | | | 25 |
| J—CHOH—C≡C—CH$_2$—C(C$_2$H$_5$)$_2$—OSiMe$_3$ | $N_E$ | Z | A | 310 | 26 |
| J—CHOH—C≡C—CH$_2$—C(C$_2$H$_5$)$_2$—OSiMe$_3$ | $N_E$ | Z | B | 311 | 26 |
| J—CHOH—C≡C—CH$_2$—C(C$_2$H$_5$)$_2$—OSiMe$_3$ | $N_Z$ | Z | A | 410 | 27 |

TABLE 3-continued

Some intermediate products

| Formula | N | Config. at 17(20) | Config. at C22 (A or B) | Comp. No. | Prep. No. |
|---|---|---|---|---|---|
| J—CHOH—C≡C—CH$_2$—C(C$_2$H$_5$)$_2$—OSiMe$_3$ | N$_Z$ | Z | B | 411 | 28 |
| J—CHOEt—C≡C—CH$_2$—C(C$_2$H$_5$)$_2$—OSiMe$_3$ | N$_Z$ | Z | A | 510 | 29 |
| J—CHOEt—C≡C—CH$_2$—C(C$_2$H$_5$)$_2$—OSiMe$_3$ | N$_Z$ | Z | B | 511 | 30 |
| JC$^{22}$H=CHC$^{24}$H=CH—COOEt, 22E, 24E | N$_Z$ | Z | | 312 | 32 |
| JC$^{22}$H=CHC$^{24}$H=CH—CEt$_2$—OH, 22E, 24E | N$_Z$ | Z | | 412 | 33 |
| J—CH$_2$O-(m)-C$_6$H$_4$—C(CH$_3$)$_2$—OH | N$_E$ | Z | | 313 | 35 |
| J—CH$_2$O-(m)-C$_6$H$_4$—C(CH$_3$)$_2$—OH | N$_Z$ | Z | | 413 | 36 |
| J—CH$_2$—O—(CH$_2$)$_3$—C(C$_2$H$_5$)$_2$—OSiMe$_3$ | N$_E$ | Z | | 314 | 37 |
| J—CH$_2$—O—(CH$_2$)$_3$—C(C$_2$H$_5$)$_2$—OSiMe$_3$ | N$_Z$ | Z | | 414 | 38 |
| J—CH$_2$OH—(CH$_2$)$_3$—C(C$_2$H$_5$)$_2$—OSiMe$_3$ | N$_E$ | Z | A | 315 | 39 |
| J—CH$_2$OH—(CH$_2$)$_3$—C(C$_2$H$_5$)$_2$—OSiMe$_3$ | N$_E$ | Z | B | 316 | 39 |
| J—CH$_2$OH—(CH$_2$)$_3$—C(C$_2$H$_5$)$_2$—OSiMe$_3$ | N$_Z$ | Z | A | 415 | 40 |
| J—CH$_2$OH—(CH$_2$)$_3$—C(C$_2$H$_5$)$_2$—OSiMe$_3$ | N$_Z$ | Z | B | 416 | 41 |
| J—CH$^{22}$=CH$^{23}$—CO—C(CH$_2$)$_2$, 22E | N$_Z$ | Z | | 317 | 42 |
| J—CH$^{22}$=CH$^{23}$CHOH—C(CH$_2$)$_2$, 22E | N$_Z$ | Z | | 417 | 43 |

J: See Scheme 2

N (N$_E$/N$_Z$): See Scheme 1

Configuration at C22: Isomer A is, or is derived from, the less polar A isomer at the N$_E$-intermediate stage; isomer B is, or is derived from, the corresponding more polar B isomer at the N$_E$-intermediate stage.

Configuration at C22: Isomer A is the 22 isomer of compound I derived from the less polar A isomer at the N$_E$-intermediate stage; isomer B is the 22 isomer of compound I derived from the corresponding more polar B isomer at the N$_E$-intermediate stage, (cf. Table 3).

General Procedure

Photoisomerisation

A solution of the appropriate compound (N=N$_E$) (0.28 mmol), anthracene (0.1 g) and triethylamine (0.20 ml, 1.4 mmol) in dichloromethane (16 ml) in a 25 ml round-bottomed Pyrex flask was irradiated at ca. 10° C. with UV-light from a high pressure ultraviolet lamp, type TQ760Z2 (Hanau), at 700 W, for 30 minutes (15 minutes at 0.08 mmol scale) while stirring. The reaction mixture was evaporated in vacuo, and the residue was treated with petroleum ether (2×2 ml) and filtered. The filtrate was concentrated and purified by chromatography to afford the compound where N=N$_Z$.

Variation: General Procedure 1a

The procedure of General Procedure 1 was followed, except that 9-acetylanthracene was used instead of anthracene, and 45 minutes with a TQ150Z2 lamp (Hanau) was used, instead of the lamp and time in General Procedure 1.

Variation: General Procedure 1b

The procedure of General Procedure 1 was followed, except that 9-acetylanthracene (25 mg) was used instead of anthracene, toluene (20 ml) was used instead of dichloromethane, and the lamp was used at 500 W for 10 minutes (5 minutes at 0.05 mmol scale) instead of 700 W for 30 minutes.

General Procedure 2

Deprotection with HF

To a stirred solution of the appropriate silyl-protected compound (0.25 mmol) in ethyl acetate (1.5 ml) was added acetonitrile (6 ml) followed by a 5% solution of hydrofluoric acid in acetonitrile-H$_2$O 7:1 (2.0 ml). After stirring for a further 45–60 minutes, 1 M potassium hydrogen carbonate (10 ml) was added, and the reaction mixture was worked up

TABLE 4

Exemplified Compounds I

| Formula | Config. at C22 | Comp. No. | Exam. No. | General Method of Synthesis |
|---|---|---|---|---|
| D$_Z$—CHOH—C$_4$H$_9$ | A | 101 | 1 | 2 |
| D$_Z$—CHOH—C$_4$H$_9$ | B | 102 | 2 | 2 |
| D$_Z$—(CH$_2$)$_3$CH(CH$_3$)$_2$ | | 103 | 3 | 1 |
| D$_Z$—CHOH—C≡C—CH$_2$—C(C$_2$H$_5$)$_2$OH | A | 104 | 4 | 4 |
| D$_Z$—CHOH—C≡C—CH$_2$—C(C$_2$H$_5$)$_2$OH | B | 105 | 5 | 4 |
| D$_Z$—CHOC$_2$H$_5$—C≡C—CH$_2$—C(C$_2$H$_5$)$_2$OTHP | A | 106 | 6 | 4 |
| D$_Z$—CHOC$_2$H$_5$—C≡C—CH$_2$—C(C$_2$H$_5$)$_2$OTHP | B | 107 | 7 | 4 |
| D$_Z$—(CH$_2$)$_3$C(CH$_3$)$_2$OH | | 108 | 8 | 1 |
| D$_E$—(CH$_2$)$_3$C(CH$_3$)$_2$OH | | 109 | 9 | 1 |
| D$_Z$—CHOC$_2$H$_5$—C≡C—CH$_2$—C(C$_2$H$_5$)$_2$OH | A | 110 | 10 | 4 |
| D$_Z$—CHOC$_2$H$_5$—C≡C—CH$_2$—C(C$_2$H$_5$)$_2$OH | B | 111 | 11 | 4 |
| D$_Z$—C$^{22}$H=CHC$^{24}$H=CH—C(C$_2$H$_5$)$_2$OH, 22E, 24E | | 112 | 12 | 6 |
| D$_Z$—CH$_2$—O-(m)C$_6$H$_4$—C(CH$_3$)$_2$OH | | 113 | 13 | 7 |
| D$_Z$—CH$_2$—O—(CH$_2$)$_3$—C(C$_2$H$_5$)$_2$OH | | 114 | 14 | 7 |
| D$_Z$—CH$_2$OH—(CH$_2$)$_3$—C(C$_2$H$_5$)$_2$OH | A | 115 | 15 | 2 |
| D$_Z$—CH$_2$OH—(CH$_2$)$_3$—C(C$_2$H$_5$)$_2$OH | B | 116 | 16 | 2 |
| D$_Z$—CH$^{22}$=CH$^{23}$CHOH—C(CH$_2$)$_2$, 22E | | 117 | 17 | 5 |

D (D$_Z$/D$_E$): See Scheme 3

(ethyl acetate). The residue was purified by chromatography (eluant: 30% pentane in ethyl acetate) to give the desired compound I.

General Procedure 3

Deprotection with TBAF

To a solution of the appropriate silyl-protected compound (0.18 mmol) in THF (4.5 ml) was added TBAF trihydrate (0.29 g, 0.9 mmol), and the mixture was heated to reflux for one hour with stirring. After addition of 0.2 M sodium hydrogen carbonate (5 ml), the mixture was worked up (ethyl acetate). The residue was purified by chromatography (eluant: 30% pentane in ethyl acetate) to yield the desired compound I.

| General Procedure 4 (C.f. Method 4) | Reaction of a Compound IIa with an acetylenic side chain building block |
|---|---|

To a solution of the appropriate acetylenic side chain building block (3.0 mmol) in dry THF (5 ml), cooled to −78° C. and stirred under argon, was added dropwise, during 2 minutes, a solution of n-butyllithium (1.6 M in hexane; 1.5 ml). Stirring was continued at −78° C. for 15 minutes and then at 20° C. for another 15 minutes. The mixture was again cooled to −78° C., and a solution of the appropriate aldehyde, compound IIa, (1.5 mmol) in dry THF (5 ml) was added dropwise during 4 minutes, and after that, stirring was continued at −78° C. for 30 minutes. The reaction mixture was worked up (ether) to yield a crude product containing the isomeric 22-hydroxy compounds A (less polar) and B (more polar). These were separated by chromatography (mixture of ethyl acetate and petroleum ether as eluant) to yield the pure compounds.

| General Procedure 5 (C.f. Method 4) | Alkylation of an acetylenic C-22-hydroxy-compound ($R^3$ = H) to the corresponding compound where $R^3$ = $C_1$–$C_5$ |
|---|---|

To a solution of the appropriate 22-hydroxy compound ($R^3$=H) (0.5 mmol) in dry THF (5 ml) was added, while stirring at 20° C. under argon, a 20% suspension of potassium hydride in mineral oil (0.2 ml) followed by an alkylating agent, $R^3Y$ (1.5 mmol). Then, a solution of 18-Crown-6 (0.13 g) in dry THF (2 ml) was added, during 5 minutes. Stirring at 20° C. was continued for two hours, after which the reaction mixture was worked up (ether). The crude product was purified by chromatography (mixture of ether and petroleum ether as eluant) to yield the desired alkoxy compound.

Preparation 1

Compounds 201 and 202

To a solution of 1(S),3(R)di(tert-butyidimethylsilyloxy)-20(S)-formyl-9,10-secopregna-5(E),7(E),10(19),16-tetraene (W. von Daehne et al., poster at X vit. D workshop, Strasbourg 1997; WO 98/24762) (3; N=$N_E$, 20S-isomer) (2.28 g, 4 mmol) in dichloromethane (20 ml) was added with stirring TBABr (258 mg, 0.8 mmol) followed by 2N aqueous sodium hydroxide (10 ml). After stirring at room temperature for 40 minutes, the mixture was diluted with dichloromethane (20 ml) and water (30 ml). The organic phase was separated and the aqueous layer extracted with dichloromethane (40 ml). The combined organic extracts were washed with water (4×25 ml) and brine (25 ml), dried over magnesium sulfate end evaporated in vacuo to yield a mixture of compounds 201 (Z-form) and 202 (E-form) in an approximate molar ratio of 95:5. Separation of the two compounds was performed by chromatography on silica gel (eluant: 2.5 to 5% ether in petroleum ether) to give the less polar Z-isomer 201 and the more polar E-isomer 202, both as colourless crystals (from ether-methanol).

Compound 201

$^1$H NMR δ 0.06 (m,12H), 0.85 (s,9H), 0.90 (s,9H), 0.95 (s,3H), 1.70 (bs,3H), 1.50–2.70 (m,14H), 2.87 (m,1H), 4.23 (m,1H), 4.53 (m,1H), 4.96 (m,1H), 4.99 (m,1H), 5.92 (d,1H), 6.43 (d,1H), 10.2 (s,1H). M.p. 113–114° C.; Anal. Calcd. for $C_{34}H_{58}O_3Si_2$: C, 71.52, H, 10.24. Found: C, 71.51, H, 10.19. UV (EtOH, nm): $\lambda_{max}$ 265 (ε 35900); IR (KBr) 1665, 1620 cm$^{-1}$.

Compound 202

$^1$H NMR δ 0.06 (m,12H), 0.83 (s,3H), 0.84 (s,9H), 0.89 (s,9H), 1.80 (bs, 3H), 1.50–2.0 (m,8H), 2.23 (dd, 1H), 2.33 (m,2H) 2.57 (dd, 1H), 2.88 (m,2H), 3.09 (dd,1H), 4.22 (m,1H), 4.53 (m,1H), 4.96 (m,1H), 4.99 (m,1H), 5.91 (d,1H), 6.44 (d,1H), 9.99 (s,1H). M.p. 109–110° C.; EIMS calcd. for $C_{34}H_{58}O_3Si_2{}^+$570.3925, found 570.39. UV (EtOH, nm): $\lambda_{max}$ 268 (ε37500); IR (KBr) 1670, 1620 cm$^{-1}$.

Preparation 2

Compounds 201 and 202

By substituting 1(S),3(R)-di(tert-butyidimethylsilyioxy)-20(R)-formyl-9-10-secopregna-5(E),7(E),10(19),16-tetraene (W. von Daehne et al., poster at X vit. D workshop, Strasbourg 1997; WO 98/24762) (3; N=$N_E$, 20R-isomer) for the corresponding 20S isomer in the procedure of Preparation 1, a similar mixture of compounds 201 and 202 (approximate molar ratio 95:5) was obtained.

Preparation 3

Compounds 211 and 212

Potassium cyanide (7.0 g) (toxic) was stirred in an ice cold solution of 1(S),3(R)-di(tert-butyidimethylsilyloxy)-20-oxo-9,10-secopregna-5(E),7(E), 10(19)-triene; 1b (N=$N_E$) (K. Hansen et al., in: Vitamin D: Gene Regulation, Structure-Function Analysis and Clinical Application; Norman, A. W., Bouillon, R., Thomasset, M., Eds.; de Gruyter, Berlin, 1991, pp 161–162)(3.0 g) in a mixture of ethanol (30 ml) and acetic acid (15 ml) for 30 min. After stirring for 21 h at room temperature the mixture was filtered. Water (45 ml) was added to the filtrate and the precipitate was collected and dried in vacuo. The precipitate was dissolved in dry pyridine (5 ml) and phosphorous oxychloride (1.3 g) was added at 0° C. After stirring for 22 h at room temperature the reaction mixture was partitioned between water (150 ml) and ether (150 ml). The organic phase was washed with water (150 ml) and brine (100 ml), dried with magnesium sulfate and evaporated to dryness in vacuo. Chromatography on silica gel with methylene chloride/petroleum ether 2:1 gave the separated products, compound 211 (E-form) and compound 212 (Z-form), in the ratio of approximately 3:1.

Compound 211

$^{13}$C NMR δ 169.7, 153.3, 140.1, 136.5, 121.0, 120.0, 117.6, 106.7, 99.8, 69.9, 67.0, 55.9, 48.8, 43.7, 36.4, 36.2, 32.7, 28.2, 25.6, 25.6, 22.9, 22.5, 18.0, 17.9, 15.8, 15.3, −5.0, −5.1, −5.1.

Compound 212

$^{13}$C NMR δ 170.4, 153.3, 140.6, 136.3, 121.1, 119.2, 117.3, 106.8, 97.2, 70.0, 67.0, 55.5, 48.4, 43.7, 36.5, 35.2, 30.5, 28.4, 25.6, 25.6, 22.9, 22.0, 18.0, 17.9, 17.8, 16.7, −5.0, −5.1, −5.1.

Preparation 4

Compound 202

A solution of compound 211 (50 mg) in toluene (2 ml) was cooled to −78° C. and a solution of DIBAH (83 μl, 20% in hexane) was added. After stirring at −78° C. for 30 min and at room temperature for 27 h the mixture was stirred with saturated aqueous ammonium chloride (4 ml) for 30 min. The mixture was extracted with ethyl acetate (30 ml). The organic phase was washed with water (20 ml) and brine (20 ml), dried with magnesium sulfate and evaporated to dryness in vacuo. Chromatography on silica gel with ether/petroleum ether 1:10 gave the title compound.

$^{13}$C NMR δ 193.4, 171.9, 153.3, 140.6, 136.3, 127.9, 121.1, 117.5, 106.7, 70.0, 67.0, 54.6, 49.8, 43.7, 36.5, 36.4, 28.3, 28.2, 25.7, 25.6, 23.0, 18.0, 17.9, 15.4, 10.0, −5.0, −5.1, −5.1.

Preparation 5

Compound 203

To a stirred solution of compound 201 (366 mg, 0.64 mmol) in THF (3 ml) was subsequently added at 0° C. 0.4 M methanolic cerium (III) chloride heptahydrate (1.6 ml), methanol (3 ml) and sodium borohydride (60.8 mg, 1.6 mmol). After stirring at 0° C. for 40 minutes, the reaction mixture was diluted with ethyl acetate (40 ml) and water (15 ml) was added. The organic phase was separated, washed with water (10 ml) and brine (10 ml), dried over magnesium sulfate and evaporated in vacuo. The residual oil was purified by chromatography on silica gel (eluant: 5% ethyl acetate in petroleum ether) to give the title compound as a colourless oil.

1H NMR δ 0.05 (m,12H), 0.75 (s,3H), 0.85 (s,9H), 0.89 (s,9H), 1.69 (bs, 3H), 2.46–0.60 (m,14H), 2.56 (dd,1H), 2.84 (dd,1H), 3.95 (d,1H), 4.22 (m,1H), 4.34 (d,1H), 4.53 (m,1H), 4.94 (m,1H), 4.98 (m,1H), 5.87 (d,1H), 6.44 (d,1H).

Preparation 6

Compound 204

By substituting compound 202 for the compound 201 in the procedure of Preparation 5, the isomeric compound 204 was obtained.

1H NMR δ 6.44(d,1H), 5.86(d,1H), 4.98(m,1H), 4.94(m, 1H), 4.53(m,1H), 4.22(m,1H), 4.04(s,2H), 2.84(m,1H), 2.56 (dd,1H), 2.60–0.60(m,14H), 1.79(bs,3H), 0.89(s,9H), 0.85 (s,9H), 0.75(s,3H), 0.05(m,12H).

Preparation 7

Compounds 301 and 302

A stirred solution of compound 201 (17.1 mg, 0.03 mmol) in dry THF (2 ml) was cooled to −78° C. and 1.6 M butyl lithium in hexane (0.04 mmol) was added via a syringe. After stirring at −78° C. for a further 20 minutes, the reaction was quenched with a few drops of water and warmed to room temperature. The reaction mixture was diluted with ether (20 ml), washed with water (4×5 ml), dried over magnesium sulfate and evaporated in vacuo to give a mixture of the compounds 301 (less polar, isomer A) and 302 (more polar, isomer B) in an approximate molar ratio of 1:2. The two isomers could be separated by chromatography on silica gel (eluant: 10% ether in petroleum ether).

Compound 301

1H NMR δ 0.05 (m,12H), 0.80 (s,3H), 0.85 (s,9H), 0.89 (s,9H), 1.55 (bs,3H), 2.45–0.62 (m,23H), 2.57 (m,1H), 2.85 (m,1H), 4.22 (m,1H), 4.53 (m,1H), 4.70 (m,1H), 4.94 (m,1H), 4.98 (m,1H), 5.87 (d,1H), 6.44 (d,1H).

Compound 302

1H NMR δ 0.05 (m,12H), 0.73 (s,3H), 0.85 (s,9H), 0.89 (s,9H), 1.55 (bs,3H), 2.450.62 (m,23H), 2.57 (m,1H), 2.85 (m,1H), 4.22 (m,1H), 4.53 (m,1H), 4.70 (m,1H), 4.94 (m,1H), 4.98 (m,1H), 5.87 (d,1H), 6.44 (d,1H).

Preparation 8

Compound 401

Method: General Procedure 1

Starting material: Compound 301

Preparation 9

Compound 402

Method: General Procedure 1

Starting material: Compound 302

Preparation 10

Compound 205

To a solution, maintained at about 5° C., of pyridine (0.2 ml), DMAP (15 mg) and compound 203 (0.070 g, 0.12 mmol) in dry dichloromethane (2 ml) was added in one portion pivaloyl chloride (0.060 g, 0.5 mmol). After stirring at the same temperature for 1 h, the reaction mixture was quenched with water and partitioned between ether and 5% sodium hydrogen carbonate solution. The organic layer was separated, washed with saturated sodium chloride solution, dried over anhydrous magnesium sulfate, and concentrated in vacuo to give an oil. Purification by chromatography on silica gel (15 g) (eluant: 5% ether in petroleum ether) gave the title compound as a foam.

$^{13}$C NMR δ 178.6, 153.4, 150.4, 142.0, 135.7, 121.4, 120.3, 116.8, 106.5, 70.0, 67.0, 64.8, 56.3, 47.3, 43.8, 38.6, 38.0, 36.4, 30.1, 28.4, 27.0, 25.7, 25.6, 23.4, 22.7, 18.1, 18.1, 18.0, 17.9, −5.0, −5.1, −5.1.

Preparation 11

Compound 303

To a solution, maintained at about 5° C., of the Grignard reagent prepared from magnesium (1.1 atomic equivalents) and the side chain building block 3-methyl-1-bromobutane (0.300 g, 2 mmol) in dry THF (3 ml) was added via a syringe lithium tetrachlorocuprate (1 ml of a 0.1 M solution in dry THF) followed by compound 205 (0.055 g, 0.083 mmol) in dry THF (2 ml). After stirring at the same temperature for 16 h, the reaction mixture was quenched with water and partitioned between ether and saturated ammonium chloride solution. The organic layer was separated, washed with saturated sodium chloride solution, dried over anhydrous magnesium sulfate, and concentrated in vacuo to give an oil. Purification by chromatography on silica gel (15 g) (eluant: 2% ether in petroleum ether) gave the title compound as an oil.

$^{13}$C NMR δ 153.5, 142.8, 142.8, 135.3, 126.0, 121.5, 116.4, 106.4, 70.1, 67.1, 56.7, 46.9, 43.8, 39.3, 38.3, 36.4, 34.2, 29.9, 28.6, 27.8, 26.8, 25.7, 25.6, 23.6, 22.9, 22.5, 22.4, 19.8, 18.1, 17.9, 17.7, −4.9, −5.1.

Preparation 12

Compound 403

Method: General Procedure 1a

Starting material: Compound 303

Chromatography eluant: 2% ether in petroleum ether.

Preparation 13

Compounds 304 and 305

Method: General Procedure 4

Starting material: Compound 201

Acetylenic side chain building block: 3-Ethyl-3-(tetrahydro-4H-pyran-2-yl-oxy)-5-hexyne (WO 93/19044)

Chromatography eluant: 0% to 10% ethyl acetate in petroleum ether.

Compound 304 (isomer 22A)

1H NMR δ 6.42(d,1H), 5.86(d,1H), 5.44(m,1H), 4.98(m, 1H), 4.94(m,1H), 4.81 (m,1H), 4.53(m,1H), 4.21 (m,1H), 3.96(m,1H), 3.44(m,1H), 2.83(m,1H), 2.56(dd, 1H), 2.46(m,

2H), 1.70(bs,3H), 2.42–1.37(m,24H), 0.89(s,9H), 0.84(s, 9H), 0.93–0.80(t,6H), 0.80(s,3H), 0.05(m,12H).

Compound 305 (isomer 22B)

1H NMR δ 6.42(d,1H), 5.86(d,1H), 5.49(m,1H), 4.98(m, 1H), 4.94(m,1H), 4.80(m,1H), 4.52(m,1H), 4.21(m,1H), 3.95(m,1H), 3.43(m,$_1$ H), 2.83(m,1H), 2.56(dd,1H), 2.46(m, 2H), 1.72(bs,3H), 2.41–1.36(m,24H), 0.89(s,9H), 0.84(m, 9H), 0.93–0.80(t,6H), 0.75(s,3H), 0.05(m,12H).

Preparation 14

Compound 404

Method: General Procedure 1

Starting material: Compound 304

Chromatography eluant: 0% to 5% ethyl acetate in petroleum ether.

$^{13}$C NMR δ 148.1, 147.4, 139.5, 135.4, 125.1, 122.7, 118.3, 111.1, 93.0, 82.4, 81.8, 79.9, 71.9, 67.3, 62.8, 61.8, 56.3, 46.9, 45.9, 44.6, 38.8, 32.0, 30.3, 28.4, 28.3, 26.8, 25.7, 25.6, 25.3, 23.4, 22.7, 20.1, 18.0, 17.9, 13.8, 7.7, 7.6, –4.9, –5.0, –5.3.

Preparation 15

Compound 405

Method: General Procedure 1

Starting material: Compound 305

Chromatography eluant: 0% to 5% ethyl acetate in petroleum ether.

$^{13}$C NMR δ 148.6, 148.1, 139.5, 135.4, 124.8, 122.8, 118.4, 111.1, 93.0, 82.4, 81.6, 79.8, 72.0, 67.3, 62.8, 61.3, 56.3, 47.0, 45.9, 44.6, 38.3, 32.0, 30.4, 28.4, 28.3, 26.7, 25.7, 25.6, 25.3, 23.3, 22.7, 20.1, 18.3, 18.0, 17.9, 14.5, 7.7, 7.6, –4.9, –5.0, –5.3.

Preparation 16

Compound 406

Method: General Procedure 5

Starting material: Compound 404

Alkylating agent: Ethyl bromide

Chromatography eluant: 0% to 2.5% ethyl acetate in petroleum ether.

$^{13}$C NMR δ 148.1, 147.6, 139.6, 135.4, 124.4, 122.8, 118.4, 111.2, 93.1, 93.0, 82.3, 80.3, 80.0, 72.0, 68.6, 67.3, 63.0, 62.9, 56.4, 46.9, 45.9, 44.6, 38.9, 32.1, 30.2, 28.5, 28.4, 28.3, 26.8, 25.7, 25.6, 25.4, 23.4, 22.7, 20.2, 20.2, 18.0, 17.9, 17.7, 15.1, 14.1, 7.7, 7.6, –4.8, –4.9, –5.0, –5.3.

Preparation 17

Compound 407

Method: General Procedure 5

Starting material: Compound 405

Alkylating agent: Ethyl bromide

Chromatography eluant: 0% to 2.5% ethyl acetate in petroleum ether.

$^{13}$C NMR δ 148.5, 148.1, 139.7, 135.3, 123.9, 122.8, 118.3, 111.2, 93.0, 82.5, 80.2, 79.9, 72.0, 67.9, 67.3, 62.9, 62.8, 56.3, 47.0, 45.9, 44.6, 38.0, 32.0, 30.4, 28.5, 28.4, 26.7, 25.7, 25.6, 25.3, 23.4, 22.7, 20.1, 18.3, 18.0, 17.9, 17.7, 15.2, 14.9, 7.7, 7.6, –4.9, –5.0, –5.3.

Preparation 18

Compound 206

By substituting compound 204 for compound 203 in the procedure of preparation 10, the isomeric compound 206 was obtained as a foam.

$^{13}$C NMR δ 178.5, 153.4, 148.5, 142.1, 135.6, 121.4, 120.2, 116.7, 106.5, 70.0, 67.2, 67.0, 55.9, 47.4, 43.8, 38.7, 37.4, 36.4, 28.7, 28.5, 27.1, 25.7, 25.6, 23.4, 22.9, 18.1, 17.9, 16.4, 15.3, –4.9, –5.0, –5.1, –5.1.

Preparation 19

Compound 308

By substituting 1-bromo-3-methyl-3-trimethylsilyloxybutane for 3-methyl-1-bromobutane in the procedure of preparation 11, compound 308 was obtained.

Preparation 20

Compound 309

By substituting compound 206 for compound 205 in the procedure of preparation 19, compound 309 was obtained.

Preparation 21

Compound 408

To a solution of compound 308 (1 mmol) in THF (5 ml) and ethyl alcohol (10 ml) PPTS (30 mg) was added, and the mixture was stirred for 1 hour at 25° C. under argon. After work up (ethyl acetate with an additional aqueous sodium bicarbonate extraction), the residual crude product was purified by chromatography with 30% ether in petroleum ether as eluant to give compound 408.

$^{13}$C NMR δ 153.4, 143.3, 142.7, 135.3, 125.5, 121.5, 116.5, 106.4, 70.9, 70.0, 67.0, 56.7, 46.9, 44.0, 43.7, 38.3, 36.4, 34.2, 29.9, 29.0, 28.9, 28.5, 25.7, 25.6, 23.8, 23.6, 22.9, 19.7, 18.1, 17.9, –5.0, –5.1.

Preparation 22

Compound 409

By substituting compound 309 for compound 308 in the procedure of preparation 21, compound 409 was obtained.

1H NMR δ 6.44 (d,1H), 5.85 (d,1H), 4.98 (bs,1H), 4.93 (bs,1H),4.54 (m,1H), 4.21 (m,1H), 2.83 (dd,1H), 2.58 (dd, 1H),2.4–1.10 (m,20H), 1.68 (bs,3H), 1.21 (bs,6H), 0.89 (s,9H),0.86 (s,9H), 0.77 (s,3H), 0.05 (bs,12H).

Preparation 23

Compound 508

Method: General Procedure 1

Starting material: Compound 408

Preparation 24

Compound 509

Method: General Procedure 1

Starting material: Compound 409

Preparation 25

3-Ethyl-3-trimethylsilyloxy-5-hexyne

To a solution of 3-ethyl-3-hydroxy-5-hexyne (12.6 g) (WO 93/19044), triethylamine (67 ml) and DMAP (0.47 g) in dichloromethane (150 ml) was added, with stirring at 0° C., trimethylchlorosilane (38 ml), during 10 min. Stirring was continued at 0° C. for 15 min. and at 25° C. for 45 min. The reaction mixture was worked up, and the crude product was purified by distillation in vacuo to give the title compound as an oil, b.p. 83–85° C./25 mm Hg.

$^{13}$C NMR δ 81.6, 77.9, 69.7, 31.4, 28.9, 7.9, 2.3.

Preparation 26

Compounds 310 (isomer 22A) and 311 (isomer 22B)

Method: General Procedure 4

Starting material: Compound 201

Acetylenic side chain building block: 3-Ethyl-3-trimethylsilyloxy-5-hexyne

Chromatography eluant: 2.5% ethyl acetate in petroleum ether.

Compound 310 (isomer 22A)

$^{13}$C NMR δ 153.4, 147.3, 141.9, 135.7, 125.2, 121.3, 116.8, 106.5, 82.6, 81.7, 78.1, 70.0, 67.0, 61.8, 56.4, 47.1, 43.7, 38.7, 36.4, 31.5, 30.3, 29.3, 28.4, 25.7, 25.6, 23.4, 22.8, 18.2, 18.1, 17.9, 13.9, 7.9, 2.3, –5.0, –5.1.

Compound 311 (isomer 22B)

$^{13}$C NMR δ 153.4, 148.5, 141.9, 135.7, 124.9, 121.3, 116.8, 106.5, 82.6, 81.7, 78.1, 70.0, 67.0, 61.4, 56.4, 47.1, 43.8, 38.2, 36.4, 31.5, 30.3, 29.3, 28.4, 25.7, 25.6, 23.4, 22.7, 18.4, 18.1, 17.9, 14.5, 7.9, 2.3, –5.0, –5.1, –5.1.

Preparation 27
  Compound 410 (isomer 22A)
  Method: General Procedure 1b
  Starting material: Compound 310
  Chromatography eluant: 2.5% to 5% ether in petroleum ether.
  $^{13}$C NMR δ 148.1, 147.5, 139.6, 135.4, 125.1, 122.8, 118.3, 111.2, 82.6, 81.8, 78.1, 72.0, 67.3, 61.9, 56.3, 47.0, 45.9, 44.6, 38.8, 31.5, 30.3, 29.3, 28.3, 25.7, 25.6, 23.4, 22.8, 18.1, 18.0, 18.0, 13.9, 7.9, 2.3, −4.9, −5.0, −5.3.
Preparation 28
  Compound 411 (isomer 22B)
  Method: General Procedure 1b
  Starting material: Compound 311
  Chromatography eluant: 0% to 10% ether in petroleum ether.
  $^{13}$C NMR δ 148.7, 148.1, 139.6, 135.4, 124.8, 122.8, 118.3, 111.1, 82.6, 81.6, 78.1, 71.9, 67.3, 61.4, 56.3, 47.0, 45.9, 44.6, 38.3, 31.5, 30.4, 29.2, 28.3, 25.7, 25.6, 23.3, 22.6, 18.3, 18.0, 17.9, 14.5, 7.9, 2.3, −4.9, −5.0, −5.3.
Preparation 29
  Compound 510 (isomer 22A)
  Method: General Procedure 5
  Starting material: Compound 410
  Alkylating agent: Ethyl bromide
  Chromatography eluant: 0% to 6% ether in petroleum ether.
  $^{13}$C NMR δ 148.1, 147.6, 139.7, 135.3, 124.3, 122.8, 118.3, 111.1, 82.5, 80.4, 78.2, 72.0, 68.6, 67.3, 63.0, 56.3, 46.9, 45.9, 44.6, 38.9, 31.6, 31.6, 30.1, 29.4, 28.3, 25.7, 25.6, 23.4, 22.7, 18.0, 17.9, 17.7, 15.1, 14.2, 7.9, 2.3, −4.9, −5.0, −5.3.
Preparation 30
  Compound 511 (isomer 22B)
  Method: General Procedure 5
  Starting material: Compound 411
  Alkylating agent: Ethyl bromide
  Chromatography eluant: 0% to 2% ether in petroleum ether.
  $^{13}$C NMR δ 148.5, 148.0, 139.7, 135.3, 123.9, 122.8, 118.3, 111.2, 82.7, 80.2, 78.2, 72.0, 68.0, 67.3, 62.9, 56.3, 47.0, 45.9, 44.6, 38.0, 31.6, 30.4, 29.2, 28.3, 25.7, 25.6, 23.4, 22.7, 18.3, 18.0, 17.9, 15.2, 14.9, 7.9, 2.3, −−4.9, −5.0, −5.3.
Preparation 31
  Compound 207
  Method: General Procedure 1b
  Starting material: Compound 201
  Chromatography eluant: 0% to 10% ether in petroleum ether.
  $^{13}$C NMR δ 190.9, 174.0, 148.1, 138.2, 136.2, 130.0, 122.5, 119.2, 111.1, 71.8, 67.3, 56.0, 48.8, 45.8, 44.6, 40.4, 32.4, 28.1, 25.6, 25.6, 23.3, 22.4, 19.5, 18.0, 17.9, 11.8, −4.9, −5.0, −5.2.
Preparation 32
  Compound 312
  A solution of compound 207 (0.144 g, 0.25 mmol) and 3-(methoxycarbonyl)-2-propenyl-1-idene-triphenylphosphorane in dry toluene (3 ml) was heated at 100° C. for 18 hours. After concentration in vacuo the residue was purified by chromatography, eluant: 0% to 2.5% ether in petroleum ether, to give the title compound as an oil.
  $^{13}$C NMR δ 167.7, 157.5, 148.1, 146.3, 140.6, 139.3, 135.6, 124.2, 122.7, 118.6, 118.0, 111.1, 71.9, 67.3, 56.3, 51.2, 48.0, 45.8, 44.6, 39.1, 31.8, 28.3, 25.7, 25.6, 23.4, 22.7, 18.0, 18.0, 15.6, −4.9, −5.0, −5.3.
Preparation 33
  Compound 412
  To a stirred solution of compound 312 (20 mg, 0.031 mmol) in THF (2 ml), cooled to −78° C., was added a freshly prepared 1.16 M solution of ethyl lithium in ether (0.08 ml, 0.093 mmol). Stirring at −78° C. was continued for one hour, after which water (15 ml) was added. The reaction mixture was worked up (ether) to give a crude product which was purified by chromatography, eluant: 0% to 5% ether in petroleum ether, to give the title compound as an oil.
  1H NMR δ 6.81 (d,1H), 6.3–6.0 (m,4H), 5.61 (d,1H), 5.18 (bs,1H), 4.87 (bs 1H), 4.36 (m,1H), 4.18 (m,1H), 2.80 (bd,1H), 2.5–0.9 (m,17H), 1.72 (bs,1H), 1.57 (bq,4H), 0.90 (bt,6H), 0.88 (bs,18H), 0.83 (s,3H), 0.06 (bs,12H).
Preparation 34
  Compound 208
  To a solution of N-chlorosuccinimide (21 mg) in dry dichloromethane (1.5 ml) was added a solution of dimethylsulfide (12.2 μl) in dry dichloromethane (0.9 ml), during 5 minutes, at 0° C., with stirring. Stirring was continued for 10 minutes at 0° C. and for 20 minutes at −20° C. To the reaction mixture was added a solution of compound 203 (77 mg, 0.134 mmol) in dry dichloromethane (2.0 ml) during 5 minutes, at −20° C. Stirring was continued for 45 minutes at −20° C. to −30° C. Work-up: The reaction mixture was partitioned between ethyl acetate (20 ml) and. water (20 ml). The aqueous phase was extracted with another (15 ml) portion of ethyl acetate, and the combined organic phases were extracted with water (20 ml) and saturated aqueous sodium chloride solution (10 ml), dried with sodium sulfate, and evaporated at (0–10° C.) in vacuo; all work-up-liquids were ice-cold. The crude compound 208 was used without further purification in the following step (preparation 35).
Preparation 35
  Compound 313
  To solution of 3-(2-hydroxy-2-propyl)-phenol (46 mg, 0.30 mmol)(WO 91/15475) in dry DMF (3 ml) was added a 50% sodium hydride-in-oil-dispersion (15 mg), and the mixture was stirred at 20° C. for 90 minutes. After this, it was added to the crude compound 208 of preparation 34 and the mixture was stirred at 20° C. for 3 hours, after which it was worked up (ethyl acetate). Purification by chromatography on silica gel (eluant: 0% to 20% ether in petroleum ether) gave the title compound as an oil.
  1H NMR δ 159.2, 153.4, 150.7, 150.5, 142.0, 135.6, 129.0, 121.4, 121.2, 116.8, 116.5, 112.1, 111.3, 106.6, 72.4, 70.1, 68.3, 67.0, 56.2, 47.4, 43.8, 38.1, 36.4, 31.5, 30.2, 28.4, 25.7, 25.6, 23.4, 22.7, 18.6, 18.3, 18.1, 17.9, −5.0, −5.1.
Preparation 36
  Compound 413
  Method: General Procedure 1
  Starting material: Compound 313
  Chromatography eluant: 0% to 10% ether in petroleum ether.
  1H NMR δ 7.25(m,1H), 7.09 (m,1H), 7.04 (m,1H), 6.81 (m,1H), 6.21 (d,1H), 6.06 (d,1H), 5.18 (bd,1H), 4.87 (bd, 1H), 4.65 (d,1H), 4.36 (d,1H), 4.35 (m,1H), 4.19 (m,1H), 2.78 (bd,1H), 2.5–0.9 (m,15H), 1.74 (bt,3H), 1.57 (s,6H), 0.87 (s,18H), 0.78 (s,3H), 0.05 (bs,12H).
Preparation 37
  Compound 314
  To a solution of compound 203 (80 mg, 0.140 mmol) in dry THF was added, while stirring at 20° C. under argon, a 20% suspension of potassium hydride in mineral oil (54 μl) followed by 6-bromo-3-ethyl-3-trimethylsilyloxy-hexane (WO 89/10351) (111 μl). After 5 minutes, 18-Crown-6 (39 mg) was added, and stirring at 20° C. was continued for one and a half hours, after which the reaction mixture was worked up (ether). The crude product was purified by chromatography (0% to 5% ether in petroleum ether as eluant) to yield the title compound as an oil.

$^{13}$C NMR δ 153.4, 148.5, 142.4, 135.5, 123.0, 121.4, 116.7, 106.5, 78.5, 70.7, 70.5, 70.0, 67.0, 56.3, 47.2, 43.8, 38.2, 36.4, 34.8, 31.2, 30.0, 28.4, 25.7, 25.6, 24.0, 23.5, 22.8, 18.2, 18.2, 18.1, 17.9, 8.0, 2.5, −5.0, −5.1.

Preparation 38

Compound 414

Method: General Procedure 1; except that the crude product was used in the following step (Example 14) without previous purification by chromatography.

Starting material: Compound 314

1H NMR δ 6.22(d,1H), 6.05 (d,1H), 5.18 (m,1H), 4.86 (m,1H), 4.36(m,1H), 4.18 (m,1H), 4.10 (d,1H), 3.85 (d,1H), 3.37(t,2H), 2.78 (d,1H), 2.44 (dd,1H), 2.4–2.1 (m,5H), 1.9–1.4 (m,8H), 1.63 (s,3H), 1.45 (q,4H), 0.9–0.7 (m,4H), 0.87(d, 18H), 0.81 (t,6H), 0.74 (s,3H), 0.08 (s,9H), 0.06 (s,12H).

Preparation 39

Compound 315 and Compound 316

A solution of 6-bromo-3-ethyl-3-trimethylsilyloxy-hexane (WO 89/10351) (1.375 g, 4.9 mmol) in dry THF (5 ml), was added dropwise, during 5 minutes, to magnesium turnings (118 mg, 4.9 mgAt) (previously stirred "dry" during 20 hours under argon) together with ether (1 ml), while stirring under argon at 20° C. Stirring was continued under reflux (oil bath, 75° C.) for one and a half hours to finish the formation of the Grignard reagent, and 1.0 ml of the solution was taken out by means of a syringe, while still warm (40–50° C.). This was added to a solution of compound 201 (171 mg, 0.30 mmol) in THF (2 ml), while stirring under argon at 0–5° C. Stirring was continued for 40 minutes at 20° C., after which the reaction mixture was poured onto a mixture of ether (25 ml) and water (25 ml), containing ammonium chloride (2.5 g), while stirring. The reaction mixture was worked up (ether) to yield a crude product containing the isomeric 22-hydroxy compounds: A (less polar) and B (more polar). These were separated by chromatography (0% to 10% ether in petroleum ether as eluant) to give the pure title compounds.

Compound 315 (isomer 22A)

$^{13}$C NMR δ 153.5, 146.4, 142.1, 135.6, 128.0, 121.4, 116.7, 106.5, 78.7, 70.7, 70.0, 67.0, 56.8, 47.0, 43.8, 39.6, 38.5, 36.4, 35.9, 31.4, 30.9, 30.4, 28.4, 25.7, 25.6, 23.5, 22.9, 20.2, 18.4, 18.1, 17.9, 13.0, 8.0, 2.5, −5.0, −5.1.

Compound 316 (isomer 22B)

$^{13}$C NMR δ 153.4, 148.2, 142.1, 135.7, 127.5, 121.4, 116.9, 106.5, 78.6, 70.0, 70.0, 67.0, 56.6, 46.9, 43.8, 38.5, 38.5, 36.4, 35.1, 31.3, 31.0, 30.3, 28.5, 25.7, 25.6, 23.5, 22.8, 20.3, 18.9, 18.1, 17.9, 12.9, 8.1, 8.0, 2.5, −5.0, −5.1.

Preparation 40

Compound 415 (isomer 22A)

Method: General Procedure 1

Starting material: Compound 315

Chromatography eluant: 0% to 10% ether in petroleum ether.

Preparation 41

Compound 416 (isomer 22B)

Method: General Procedure 1

Starting material: Compound 316

Chromatography eluant: 0% to 10% ether in petroleum ether.

Preparation 42

Compound 317

A solution of compound 207 (0.25 mmol) and cyclopropylcarbonyl-methylene-triphenylphosphorane (0.5 mmol) in dry toluene (3 ml) was heated at 100° C. for 18 hours. After concentration in vacuo the residue was purified by chromatography, eluant: 0% to 2.5% ether in petroleum ether, to give the title compound as an oil.

Preparation 43

Compound 417

To a stirred solution of compound 317 (0.3 mmol) in THF (1 ml) was added at 0° C. 0.4 M methanolic cerium (III) chloride heptahydrate (1 ml), methanol (1 ml) and sodium borohydride (60 mg, 1.6 mmol). After stirring at 0° C. for 40 minutes, the reaction mixture was diluted with ethyl acetate (40 ml) and water (15 ml) was added. The organic phase was separated, washed with water (10 ml) and brine (10 ml), dried over magnesium sulfate and evaporated in vacuo. The residual oil was purified by chromatography on silica gel (eluant: 5% ethyl acetate in petroleum ether) to give the title compound as a mixture of epimers at the side chain hydroxyl position which was used as such in the subsequent step (Example 17).

Example 1

1(S),3(R)-Dihydroxy-20-(1-hydroxy-1-pentyl)-9,10-secopregna-5(Z),7(E),10(99),17(20)(Z)-tetraene, Isomer 22A Compound 101

Method: General Procedure 2 or 3

Starting material: Compound 401

Example 2

1(S),3(R)-Dihydroxy-20-(1-hydroxy-1-pentyl)-9,10-secopregna-5(Z),7(E),10(19),17(20)(Z)-tetraene, Isomer 22B Compound 102

Method: General Procedure 2 or 3

Starting material: Compound 402

Example 3

1(S),3(R)-Dihydroxy-20-(4-methyl-1-pentyl)-9,10-secopregna-5(Z),7(E),10(19),17(20)(Z)-tetraene Compound 103

Method: General Procedure 2

Starting material: Compound 403

1H NMR δ 6.37(d,1H), 6.04(d,1H), 5.34(bs,1H), 5.01(bs, 1H), 4.44(m,1H), 4.23(m,1H), 2.80(dd,1H), 2.61(dd,1H), 1.56(bs,3H), 1.10–2.35 (m,22H), 0.87(d,6H), 0.73(s,3H).

Example 4

1(S),3(R)-Dihydroxy-20-(1,5-dihydroxy-5-ethyl-2-heptyn-1-yl)-9,10-secopregna-5(Z),7(E),10(19),17(20)Z-tetraene, Isomer 22A Compound 104

Method: General Procedure 3

Starting material: Compound 410

Chromatography eluant: 50% to 100% ethyl acetate in petroleum ether.

$^{13}$C NMR δ 149.8, 147.5, 141.5, 136.2, 127.5, 124.7, 119.6, 112.1, 83.5, 82.4, 75.3, 71.5, 67.4, 62.4, 58.0, 46.2, 43.7, 40.5, 32.0, 31.2, 29.7, 29.5, 24.8, 24.2, 18.3, 14.5, 8.1.

Example 5
1(S),3(R)-Dihydroxy-20-(1,5-dihydroxy-5-ethyl-2-heptyn-1-yl)-9,10-secopregna-5(Z),7(E),10(19),17(20)Z-tetraene, Isomer 22B Compound 105

Method: General Procedure 3

Starting material: Compound 411

Method of purification: Crystallisation from ether.

M.p. 161–175° C.; 1H NMR δ 6.34(d,1H), 6.05 (d,1H), 5.51 (bs,1H), 5.33 (bs,1H), 4.99 (bs,1H), 4.43 (bs, 1H), 4.22 (bs,1H), 2.79 (d,1H), 2.59 (dd,1H), 2.37 (d,2H), 2.35–1.0 (m,17H), 1.71 (s,3H), 1.55 (bq,4H), 0.86 (bt,6H), 0.76 (s,3H).

Example 6
1(S),3(R)-Dihydroxy-20-(1-ethoxy-5-ethyl-5-(tetrahydro-4H-pyran-2-yl)oxy-2-heptyn-1-yl)-9,10-secopregna-5(Z),7(E),10(19),17(20)Z-tetraene, Isomer 22A Compound 106

Method: General Procedure 3

Starting material: Compound 406

$^{13}$C NMR δ 147.6, 147.6, 141.9, 133.6, 124.7, 117.8, 111.9, 93.2, 82.6, 80.5, 80.2, 70.8, 68.8, 66.8, 63.3, 63.0, 56.6, 47.2, 45.2, 42.9, 39.0, 32.3, 30.3, 28.7, 28.6, 27.0, 25.6, 23.8, 23.1, 20.3, 17.9, 15.3, 14.4, 7.9, 7.8.

Example 7
1(S),3(R)-Dihydroxy-20-(1-ethoxy-5-ethyl-5-(tetrahydro-4H-pyran-2-yl)oxy-2-heptyn-1-yl)-9,10-secopregna-5(Z),7(E),10(19),17(20)Z-tetraene, Isomer 22B Compound 107

Method: General Procedure 3

Starting material: Compound 407

$^{13}$C NMR δ 148.4, 147.6, 142.0, 133.5, 124.8, 124.3, 117.7, 111.9, 93.2, 82.8, 80.3, 80.1, 70.8, 68.1, 66.8, 63.1, 63.0, 56.4, 47.3, 45.3, 42.9, 38.1, 32.2, 30.5, 28.7, 28.6, 26.9, 25.5, 23.7, 23.0, 20.3, 18.5, 15.4, 15.1, 7.9, 7.8.

Example 8
1(S),3(R)-Dihydroxy-20-(4-hydroxy-4-methyl-1-pentyl)-9,10-secopregna-5(Z),7(E ),10(19),17(20)(Z)-tetraene Compound 108

Method: General Procedure 2 or 3

Starting material: Compound 508

$^{13}$C NMR δ 147.6, 143.4, 142.8, 133.1, 125.7, 125.0, 117.3, 111.9, 70.8, 66.9, 56.8, 47.1, 45.3, 44.2, 42.9, 38.5, 34.4, 30.1, 29.3, 29.2, 28.9, 24.0, 23.9, 23.1, 19.9, 17.8.

Example 9
1(S),3(R)-Dihydroxy-20-(4-hydroxy-4-methyl-1-pentyl)-9,10-secopregna-5(Z),7(E),10(19),17(20)(E)-tetraene Compound 109

Method: General Procedure 2 or 3

Starting material: Compound 509

1H NMR δ 6.37 (bd,1H), 6.04 (bd,1H), 5.34 (bs,1H), 5.02 (bs,1H), 4.44 (bm,1H), 4.23 (bm,1H), 2.80 (bd,1H), 2.60 (m,2H), 2.4–1.0 (m,21H), 1.70 (bs,3H), 1.21 (s,6H), 0.73 (s,3H).

Example 10
1(S),3(R)-Dihydroxy-20-(1-ethoxy-5-ethyl-5-hydroxy-2-heptyn-1-yl)-9,10-secopregna-5(Z),7(E),10(19),17(20)Z-tetraene, Isomer 22A Compound 110

Method: General Procedure 3

Starting material: Compound 510

Chromatography eluant: 50% to 100% ethyl acetate in petroleum ether.

$^{13}$C NMR δ 148.1, 147.6, 141.8, 133.6, 124.7, 124.5, 117.8, 111.9, 82.1, 81.6, 74.0, 70.8, 68.8, 66.8, 63.4, 56.6, 47.2, 45.3, 42.9, 39.1, 30.8, 30.3, 29.9, 28.7, 23.7, 23.1, 17.9, 15.3, 14.3, 7.9.

Example 11
1(S),3(R)-Dihydroxy-20-(1-ethoxy-5-ethyl-5-hydroxy-2-heptyn-1-yl)-9,10-secopregna-5(Z),7(E),10(19),17(20)Z-tetraene, Isomer 22B Compound 111

Method: General Procedure 3

Starting material: Compound 511

Chromatography eluant: 0% to 100% ethyl acetate in petroleum ether.

$^{13}$C NMR δ 148.8, 147.6, 141.8, 133.5, 124.7, 124.0, 117.7, 111.9, 81.9, 81.8, 74.0, 70.8, 68.0, 66.8, 63.2, 56.4, 47.3, 45.2, 42.9, 38.1, 30.8, 30.5, 29.7, 28.7, 23.7, 23.0, 18.6, 15.4, 15.1, 7.9.

Example 12
1(S),3(R)-Dihydroxy-20-(5-ethyl-5-hydroxy-hepta-1(E),3(E)-dien-1-yl)-9,10-secopregna-5(Z),7(E),10(19),17(20)Z-tetraene Compound 112

Method: General Procedure 3

Starting material: Compound 412

Chromatography eluant: 25% to 50% ethyl acetate in petroleum ether.

1H NMR δ 6.81 (d,1H), 6.37 (d,1H), 6.28 (dd,1H), 6.12 (dd,1H), 6.08 (bd,1H), 5.63 (d,1H), 5.34 (bs,1H), 5.01 (bs,1H), 4.44 (m,1H), 4.24 (m,1H), 2.80 (bd,1H), 2.60 (dd,1H), 2.5–0.90 (m,16H), 1.74 (bs,3H), 1.58 (bq,4H), 0.90 (t,6H), 0.82 (s,3H).

Example 13
1(S),3(R)-Dihydroxy-20-[3-(2-hydroxy-2-propyl)-phenoxymethyl]-9,10-secopregna-5(Z),7(E),10(19),17(20)Z-tetraene Compound 113

Method: General Procedure 3

Starting material: Compound 413

Chromatography eluant: 50% to 100% ethyl acetate in petroleum ether.

1H NMR δ 7.24(m,1H), 7.10 (m,1H), 7.04 (m,1H), 6.80 (m,1H), 6.39(d,1H), 6.06 (d,1H), 5.34 (bs,1H), 5.01 (bs,1H), 4.66 (d,1H), 4.44 (m,1H), 4.37 (d,1H), 4.23 (m,1H), 2.79 (bd,1H), 2.60 (dd,1H), 2.4–0.9 (m,16H), 1.75 (bs,3H), 1.58 (s, 6H), 0.80 (s,3H).

Example 14
1(S),3(R)-Dihydroxy-20-[(3-ethyl-3-hydroxy-6-hexyl)-oxymethyl]-9,10-secopregna-5(Z),7(E),10(19),17(20)Z-tetraene Compound 114

Method: General Procedure 3

Starting material: Compound 414

Chromatography eluant: 50% to 100% ethyl acetate in petroleum ether.

$^{13}$C NMR δ 148.8, 147.6, 142.3, 133.4, 124.8, 122.9, 117.6, 111.9, 74.1, 70.8, 70.8, 66.8, 56.4, 47.3, 45.3, 42.9, 38.4, 35.4, 31.0, 30.1, 28.8, 23.9, 23.7, 23.0, 18.4, 7.9.

Example 15

1(S),3(R)-Dihydroxy-20-(1,5-dihydroxy-5 ethyl-1-heptyl)-9,10-secopregna-5(Z),7(E),10(19),17(20)Z-tetraene, Isomer 22A Compound 115

Method: General Procedure 3

Starting material: Compound 415

Chromatography eluant: 50% to 100% ethyl acetate in petroleum ether.

Example 16

1(S),3(R)-Dihydroxy-20-(1,5-dihydroxy-5 ethyl-1-heptyl)-9,10-secopregna-5(Z),7(E),10(19),17(20)Z-tetraene, Isomer 22B Compound 116

Method: General Procedure 3

Starting material: Compound 416

Chromatography eluant: 50% to 100% ethyl acetate in petroleum ether.

Example 17

1(S),3(R)-Dihydroxy-20-(3-cyclopropyl-3-hydroxy-prop-1(E)-en-1-yl)-9,10-secopregna-5(Z),7(E),10(19),17(20)(Z)-tetraene Compound 117

Method: General Procedure 3

Starting material: Compound 417

Chromatography eluant: 50% to 100% ethyl acetate in petroleum ether.

Example 18

Capsules CVontaining Compound 105

Compound 105 was dissolved in arachis oil to a final concentration of 1 µg of Compound 105/ml oil. 10 Parts by weight of gelatine, 5 parts by weight glycerine, 0.08 parts by weight potassium sorbate, and 14 parts by weight distilled water were mixed together with heating and formed into soft gelatine capsules. These were then filled each with 100 µl of Compound 105 in oil solution, such that each capsule contained 0.1 µg of Compound 105.

Example 19

Dermatological Cream Containing Compound 108

In 1 g almond oil was dissolved 0.05 mg of Compound 108. To this solution was added 40 g of mineral oil and 20 g of self-emulsifying beeswax. The mixture was heated to liquefy. After the addition of 40 ml hot water, the mixture was mixed well. The resulting cream contains approximately 0.5 µg of Compound 108 per gram of cream.

What we claim is:

1. A compound of the formula I in which formula X is hydrogen or hydroxy or protected hydroxy; $R^1$ and $R^2$ stand for hydrogen, methyl or ethyl, or, when taken together, $R^1$ and $R^2$ can form a $C_3$–$C_5$ carbocyclic ring; Q is a $C_3$–$C_6$ hydrocarbylene, hydrocarbylene indicating the diradical obtained after removal of 2 hydrogen atoms from a straight or branched, saturated or unsaturated hydrocarbon, in which one of any $CH_2$ groups may optionally be replaced by an oxygen atom or a carbonyl group, such that the carbon atom (C-22) directly bonded to C-20 is an $sp^2$ or $sp^3$ hybridized carbon atom; and in which another of the $CH_2$ groups may be replaced by phenylene, and where Q may optionally be substituted with one or more hydroxy or $C_1$–$C_4$-alkoxy groups.

2. A diastereoisomer of a compound according to claim 1, in pure form; or a mixture of diastereoisomers of a compound according to claim 1.

3. A compound according to claim 1 which is:
   a) 1(S),3(R)-Dihydroxy-20-(4-methyl-1-pentyl)-9,10-secopregna-5(Z),7(E),10(19),17(20)(Z)-tetraene
   b) 1(S),3(R)-Dihydroxy-20-(4-hydroxy-4-methyl-1-pentyl)-9,10-secopregna-5(Z),7(E),10(19),17(20)(Z)-tetraene
   c) 1(S),3(R)-Dihydroxy-20-(4-hydroxy4-methyl-1-pentyl)-9,10-secopregna-5(Z),7(E),10(19),17(20)(E)-tetraene
   d) 1(S),3(R)-Dihydroxy-20-(1,5-dihydroxy-5-ethyl-2-heptyn-1-yl)-9,10-secopregna-5(Z),7(E),10(19),17(20) Z-tetraene, both 22-isomers
   e) 1(S),3(R)-Dihydroxy-20-(1-ethoxy-5-ethyl-5-hydroxy-2-heptyn-1-yl)-9,10-secopregna-5(Z),7(E),10(19),17(20)Z-tetraene, both 22-isomers
   f) 1(S),3(R)-Dihydroxy-20-(5-ethyl-5-hydroxy-hepta-1(E),3(E)-dien-1-yl)-9,10-secopregna-5(Z),7(E),10(19),17(20)Z-tetraene
   g) 1(S),3(R)-Dihydroxy-20-[3-(2-hydroxy-2-propyl)-phenoxymethyl]-9,10-secopregna-5(Z),7(E),10(19),17(20)Z-tetraene
   h) 1(S),3(R)-Dihydroxy-20-[(3-ethyl-3-hydroxy-6-hexyl)-oxymethyl]-9,10-secopregna-5(Z),7(E),10(19),17(20)Z-tetraene
   i) 1(S),3(R)-Dihydroxy-20-(1,5-dihydroxy-5 ethyl-1-heptyl)-9,10-secopregna-5(Z),7(E),10(19),17(20)Z-tetraene, both 22-isomers
   j) 1(S),3(R)-Dihydroxy-20-(3-cyclopropyl-3-hydroxy-prop-1(E)-en-1-yl)-9,10-secopregna-5(Z),7(E),10(19),17(20)(Z)-tetraene.

4. A method for producing a compound of formula I of claim 1 by which:
  a) the side chain attached to C-20 in compound I is elaborated from 1(S),3(R)-bis-(tert-butyldimethylsilyloxy)-20-formyl-9,10-secopregna-5(E),7(E),10(19),17(20)(Z)tetraene, or from 1(S),3(R)-bis-(tert-butyldimethylsilyloxy-20-formyl-9,10-secopregna-5(E),7(E),10(19),17(20)(E)-tetraene, or their corresponding 5(Z) isomers, either
    (i) by reaction with the lithium salt of the side chain building block HC≡C(CH$_2$)$_n$CR$_2$-OPG (PG= protecting group), where n is 0, 1 or 2, R is methyl or ethyl and PG is trimethylsilyl or tetrahydropyranyl, prepared by reaction with butyllithium, in a solvent, or
    (ii) by reaction with the Grignard reagent BrMg(CH$_2$)$_n$C(R)O—Si(CH$_3$)$_3$, where n=2, 3 or 4 and R=methyl or ethyl, in a solvent, and
  b) the compound from step a), above, is optionally (i) separated from diastereoisomers, (ii) subjected to triplet-sensitized photo-isomerisation to the 5(Z) isomer, (iii) alkylated at the 22-hydroxy group with a C$_1$–C$_3$ alkyl bromide or iodide in the presence of a base and a phase transfer catalyst, in a solvent, and (iv) desilylated.

5. A pharmaceutical composition containing an effective amount of one or more of the compounds of claims 1, 2 or 3 together with pharmaceutically acceptable, non-toxic carriers and/or auxiliary agents.

6. A pharmaceutical composition according to claim 5 in dosage unit form containing from 0.1 ppm to 0.1% by weight of the dosage unit of a compound of formula I.

7. A method for inhibiting abnormal cell proliferation or for obtaining immunosuppressive activity which comprises administering to a host in need of such treatment, an effective amount of a compound according to claim 1.

* * * * *